United States Patent
Lenz et al.

(10) Patent No.: US 7,662,553 B2
(45) Date of Patent: Feb. 16, 2010

(54) POLYMORPHISMS IN THE ERCC1 GENE FOR PREDICTING TREATMENT OUTCOME

(75) Inventors: Heinz-Josef Lenz, Altadena, CA (US); Jan Stoehlmacher, Monrovia, CA (US); David (Jong-Han) Park, Rowland Heights, CA (US)

(73) Assignee: University of Southern California, Los Angeles, CA (US)

( * ) Notice: Subject to any disclaimer, the term of this patent is extended or adjusted under 35 U.S.C. 154(b) by 79 days.

(21) Appl. No.: 10/522,664

(22) PCT Filed: Jul. 31, 2003

(86) PCT No.: PCT/US03/24065

§ 371 (c)(1),
(2), (4) Date: Aug. 3, 2005

(87) PCT Pub. No.: WO2004/011625

PCT Pub. Date: Feb. 5, 2004

(65) Prior Publication Data

US 2006/0094012 A1 May 4, 2006

Related U.S. Application Data

(60) Provisional application No. 60/400,276, filed on Jul. 31, 2002, provisional application No. 60/400,253, filed on Jul. 31, 2002, provisional application No. 60/400,250, filed on Jul. 31, 2002, provisional application No. 60/400,249, filed on Jul. 31, 2002.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/6; 435/91.2; 536/23.5; 536/24.31; 436/63; 436/64

(58) Field of Classification Search ........................ None
See application file for complete search history.

(56) References Cited

U.S. PATENT DOCUMENTS

| | | | |
|---|---|---|---|
| 5,705,336 | A | 1/1998 | Reed et al. |
| 5,985,561 | A | 11/1999 | Kimberly et al. |
| 6,573,052 | B2 | 6/2003 | Danenberg |
| 6,602,670 | B2 | 8/2003 | Danenberg |
| 6,716,581 | B2 | 4/2004 | Lenz et al. |
| 7,049,059 | B2 | 5/2006 | Danenberg |
| 7,132,238 | B2 | 11/2006 | Danenberg |
| 2004/0067519 | A1 | 4/2004 | Lenz et al. |
| 2004/0265813 | A1 | 12/2004 | Takechi et al. |
| 2005/0064417 | A1 | 3/2005 | Watier et al. |
| 2006/0008825 | A1 | 1/2006 | Levy et al. |
| 2006/0115827 | A1 | 6/2006 | Lenz |
| 2006/0121526 | A1 | 6/2006 | Danenberg |
| 2007/0207486 | A1 | 9/2007 | Lenz |
| 2007/0218487 | A1 | 9/2007 | Lenz |
| 2007/0244083 | A1 | 10/2007 | Lenz |

FOREIGN PATENT DOCUMENTS

| | | |
|---|---|---|
| WO | WO 01/36686 A2 | 5/2001 |
| WO | WO 01/36686 A3 | 5/2001 |
| WO | WO 01/75175 A2 | 10/2001 |
| WO | WO 01/75175 A3 | 10/2001 |
| WO | WO 01/75175 R5 | 10/2001 |
| WO | WO 02/057489 | 7/2002 |
| WO | WO 02/061128 | 8/2002 |
| WO | WO 2004/011625 A2 | 2/2004 |
| WO | WO 2004/011625 A3 | 2/2004 |
| WO | WO 2004/037852 A2 | 5/2004 |
| WO | WO 2007/064957 | 6/2007 |
| WO | PCT/US2008/000650 | 1/2008 |
| WO | PCT/US2008/000651 | 1/2008 |
| WO | PCT/US2008/000660 | 1/2008 |
| WO | PCT/US2008/000661 | 1/2008 |
| WO | PCT/US2008/000685 | 1/2008 |
| WO | PCT/US2008/000715 | 1/2008 |
| WO | PCT/US2008/051527 | 1/2008 |

OTHER PUBLICATIONS

Hirschhorn et al. Genetics in Medicine. 2002. 4(2): 45-61.*
Halushka et al. Nature. Jul. 1999. 22: 239-247.*
Yu et al. Mutation Research. 1997. 382: 13-20.*
Yu et al. Cancer Letters. 2000. 151: 127-132.*
Winter et al. Oncogene. 2005. 24: 2110-2113.*
Lee et al. Proceedings American Association Cancer Research. 2005. 46: Abstract 1496.*
Grau et al. Journal of Clinical Oncology. 2005. 23: 511S.*
Viguier et al. Clinical Cancer Research. 2005. 11: 6212-6217.*
Britten et al. International Journal of Cancer. 2000. 89: 453-457.*
Kang et al. Experimental and Molecular Medicine. 2006. 38: 320-.*
Culy et al. Drugs. Oct. 2000. 60(4): 895-924.*
Abdel-Rahman, S. et al. "Polymorphisms in DNA Repair Gene XRCC1 Increases the Risk of Colorectal Cancer in Egypt" *Proceedings of the American Association for Cancer Research* (Mar. 2000) 41:595, No. 3791.
Board, P.G. et al. "Isolation of a cDNA clone and localization of the humnan glutathione S-transferase 3 genes to chromosome bands 11q13 and 12q13-14" *Ann. Hum. Genet.* (1989) 53:205-213.
Caldecott, K.W. et al. "XRCC1, A Central Regulator of Single Strand Break Repair and Base Excision Repair" *Proceedings of the American Association for Cancer Research* (Mar. 2000) 41:891, No. 526.
Duell, E.J. et al. "Polymorphisms in the DNA repair genes *XRCC1* and *ERCC2* and biomarkers of DNA damage in human blood mononuclear cells" *Carcinogenesis* (May 2000) 21(5):965-971.

(Continued)

Primary Examiner—Carla Myers
(74) Attorney, Agent, or Firm—Antoinette F. Konski; Foley & Lardner LLP

(57) ABSTRACT

The invention provides compositions and methods for determining the increased risks for recurrence of certain cancers and the likelihood of successful treatment with one or both of chemotherapy and radiation therapy. The methods comprising determining the type of genomic polymorphism present in a predetermined region of the gene of interest isolated from the subject or patient. Also provided are nucleic acid probes and kits for determining a patient's cancer risk and treatment response.

12 Claims, 4 Drawing Sheets

OTHER PUBLICATIONS

Divine, K.K. et al. "The XRCC1 399 GLN Polymorphism:. Potential Association with Lung Adenocarcinoma" *Proceedings of the American Association for Cancer Research* (Mar. 2000) 41:591, No. 3762.

Edler, D. et al. "Thymidylate Synthase Expression: An Independent Prognostic Factor for Local Recurrence, Distant Metastasis, Disease-free and Overall Survival in Rectal Cancer" *Clinical Cancer Research* (Apr. 2000) 6:1378-1384.

Halpern, J. "Maximally Selected Chi Square Statistics for Small Samples" *Biometrics* (Dec. 1982) 38:1017-1023.

Harries, L.W. et al. "Identification of genetic polymorphisms at the glutathione S-transferase Pi locus and association with susceptibility to bladder, testicular and prostate cancer" *Carcinogenesis* (1997) 18(4):641-644.

Heidelberger, C. et al. "Fluorinated Pyrimidines, A New Class of Tumour-Inhibitory Compounds" *Nature* (Mar. 30, 1957) 179:663-666.

Horie, N. et al. "Functional Analysis and DNA Polymorphism of the Tandemly Repeated Sequences in the 5'-terminal Regulatory Region of the Human Gene for Thymidylate Synthase" *Cell Structure and Function* (1995) 20:191-197.

Horikoshi, T. et al. "Quantitation of Thymidylate Synthase, Dihydrofolate Reductase, and DT-Diaphorase Gene Expression in Human Tumors Using the Polymerase Chain Reaction" *Cancer Res.* (Jan. 1, 1992) 52:108-116.

Howie, A.F. et al. "Glutathione S-transferase and glutathione peroxidase expression in normal and tumour human tissues" *Carcinogenesis* (1990) 11(3):451-458.

Hu, J.J. et al. "Genetic Polymorphism of DNA Repair in Human Prostate Cancer Risk" *Proceedings of the American Association for Cancer Research* (Mar. 2000) 41:596, No. 3798.

Ishikawa, Y. et al. "Dihydropyrimidine Dehydrogenase Activity and Messenger RNA Level May Be Related to the Antitumor Effect of 5-Fluorouracil on Human Tumor Xenografts in Nude Mice" *Clin. Cancer Res.* (Apr. 1999) 5:883-889.

Leichman, C.G. et al. "Quantitation of Intratumoral Thymidylate Synthase Expression Predicts for Disseminated Colorectal Cancer Response and Resistance to Protracted-Infusion Fluorouracil and Weekly Leucovorin" *J. Clinical Oncology* (Oct. 1997) 15(10):3223-3229.

Mannervik, B. "The Isoenzymes of Glutathione Transferase" *Adv. Enzymol.* (1985) 57:357-417.

Miller, R. and D. Siegmund "Maximally Selected Chi Square Statistics" *Biometrics* (Dec. 1982) 38:1011-1016.

Moscow, J.A. et al. "Expression of Anionic Glutathione-S-transferase and P-Glycoprotein Genes in Human Tissues and Tumors" *Cancer Res.* (Mar. 15, 1989) 49:1422-1428.

Nishimura, T. et al. "Association between expression of glutathione-associated enzymes and reponse to platinum-based chemotherapy in head and neck cancer" *Chemico-Biological Interactions* (1998) 111-112:187-198.

Peters, W.H.M. et al. "Expression of Drug-Metabolizing Enzymes and P-170 Glycoprotein in Colorectal Carcinoma and Normal Mucosa" *Gastroenterology* (Aug. 1992) 103:448-455.

Salonga, D. et al. "Colorectal Tumors Responding to 5-Fluorouracil Have Low Gene Expression Levels of Dihydropyrimidine Dehydrogenase, Thymidylate Synthase, and Thymidine Phosphorylase" *Clin. Cancer Res.* (Apr. 2000) 6:1322-1327.

Singh, S.V. et al. "Differential expression of glutathione S-transferase, glutathione peroxidase, and glutathione reductase in normal and malignant human breast tissues" *Cancer Letters* (1990) 51:43-48.

Stern, M.C. et al. "DNA Repair Gene XRCC1 Polymorphisms, Smoking and Bladder Cancer Risk" *Proceedings of the American Association for Cancer Research* (Mar. 2000) 41:592, No. 3771.

Sweeney, C. et al. "Association between Survival after Treatment for Breast Cancer and Glutathione S-Transferase P1 Ile$^{105}$Val Polymorphism" *Cancer Res.* (Oct. 15, 2000) 60:5621-5624.

Terrier, P. et al. "An Immunohistochemical Study of Pi Class Glutathione S-Transferase Expression in Normal Human Tissue" *Am. J. Pathol.* (Oct. 1990) 137(4):845-853.

Tsuchida. S. and K. Sato "Glutathione Transferases and Cancer" *Rev. Biochem. Mol. Biol.* (1992) 27(4,5):337-384.

van Lieshout, E.M.M. "Polymorphic Expression of the Glutathione S-Transferase *P1* Gene and Its Susceptibility to Barrett's Esophagus and Esophageal Carcinoma" *Cancer Res.* (Feb. 1, 1999) 59(3):586-589.

Watson, M.A. et al. Human glutathione *S*-transferase P1 polymorphisms: relationship to lung tissue enzyme activity and population frequency distribution *Carcinogenesis* (1998) 19(2):275-280.

Wei, X. et al. "Molecular Basis of the Human Dihydropyrimidine Dehydrogaenase Deficiency and 5-Fluorouracil Toxicity" *J. Clinical Investigations* (Aug. 1996) 98(3):610-615.

Zimniak, P. et al. "Naturally occurring human glutathione *S*-transferase GSTP1-1 isoforms with isoleucine and valine in position 104 differ in enzymic properties" *Eur. J. Biochem.* (1994) 224:893-899.

International Search Report for PCT/US2003/024065 dated Sep. 27, 2004.

Iacopetta, B. et al. "A Polymorphism in the Enhancer Region of the Thymidylate Synthase Promoter Influences the Survival of Colorectal Cancer Patients Treated with 5-Fluorouracil" *British Journal of Cancer*, London, GB (Sep. 14, 2001) 85(6):827-830.

Lenz, Heinz-Josef et al. "A 6 base-pair deletion in the 3 UTR of the thymidylate synthase (TS) gene predicts TS mRNA expression in colorectal tumors: A possible candidate gene for colorectal cancer risk" *Proceedings of the American Association for Cancer Research Annual Meeting* (Mar. 2002) 43:660.

Park, David J. et al. "Thymidylate synthase gene polymorphism predicts response to capecitabine in advanced colorectal cancer" *International Journal of Colorectal Disease* (Jan. 2002) 17(1):46-49.

Pullarkat, S. et al. "Thymidylate Synthase Gene Polymorphism Determines Response and Toxicity of 5-FU Chemotherapy" *Pharmacogenomics Journal* (2001) 1(1):65-70.

Shirota, Y. et al. "ERCC1 and Thymidylate Synthase MRNA Levels Predict Survival for Colorectal Cancer Patients Receiving Combination Oxaliplatin and Fluorouracil Chemotherapy" *Journal of clinical Oncology* (Dec. 1, 2001) 19(23):4298-4304.

Ulrich et al. "Searching Expressed Sequence Tag Databases: Discovery and Confirmation of a Common Polymorphism in the Thymidylate Synthase Gene" *Cancer Epidemiology, Biomarkers & Prevention* (2000) 9:1381-1385.

Villafranca et al. "Polymorphisms of the Repeated sequences in the Enhancer Region of the Thymidylate Synthase Gene Promoter May Predict Downstaging After Preoperative Chemoradiation in Rectal Cancer" (2001) *Journal of Clinical Oncology* 19(6):1779-1786.

European Search Report for EP 03 77 2163 dated Oct. 4, 2005.

Kuniyasu et al. "Induction of angiogenesis by hyperplastic colonic mucosa adjacent to colon cancer" *American Journal of Pathology* (Nov. 2000) 157(5):1523-1535.

Fox et al. "Angiogenesis in normal tissue adjacent to colon cancer" *Journal of Surgical Oncology* (Dec. 1998) 69(4):230-234.

Liotta et al. "The microenvironment of the tumour-host interface" *Nature* (May 2001) 411(6835):375-379.

European Search Report for EP 03772163.6 dated Feb. 3, 2006.

Promega Catalog (1997) p. 78.

U.S. Appl. No. 09/715,764, filed Nov. 15, 2000, Lenz et al.

Iqbal and Lenz (2001) "Determinants of prognosis and response to therapy in colorectal cancer," *Curr. Oncol. Rep.* 3(2):102-108.

Iqbal et al. (2003) "Targeted therapy and pharmacogenomic programs" *Cancer* 97:2076-2082.

Iqbal et al. (2003) "Molecular predictors of treatment and outcome in colorectal cancer," Curr Gastroenterol Rep 5(5):399-405.

Iyer and Ratain (1998) "Pharmacogenetics and cancer chemotherapy" Eur. J. Cancer 34:1493-1499.

Lenz (2002) "Pharmacogenetic determinants of clinical outcome and toxicity in colon cancer," *Eur J Cancer* 38(Suppl. 7):S68 #212.

Lenz (2003) "Pharmacogenomics in colorectal cancer," *Semin Oncol.* 30(4 Suppl 15):47-53.

Lenz et al. (1997) "Molecular markers as indicators of response and outcome in primary gastric cancer" Prog Gastric Cancer Res 2:1295-1300.

Lenz et al. (1998) "Thymidylate synthase (TS) and ERCC1 MRNA expression in patients with inflammatory bowel disease (IBD)," Proc ASCO 17:562a.

Lenz et al. (2002) A multivariate analysis of genetic markers for clinical response to 5-FU/oxaliplatin chemotherapy in advanced colorectal cancer. Proc ASCO 21:513.

Lenz et al. (2003) "Gene expression profile in normal tissue predicts pelvic recurrence in patients with rectal cancer treated with adjuvant chemoradiation therapy," Proc ASCO 22:1185.

Leong et al. (2003) "Ribonucleotide reductase M1 and M2 (RR-M1, -M2), cytidine deaminase (CDA), deoxycytidine deaminase (dCDA), deoxycytidine kinase (dCK), and excision repair cross complementation—1 (ERCC-1) expression in advanced malignancies treated with combined oxaliplatin and gemcitabine," Onkologie 26(3):p. 46, A3456.

Leong et al. (2003) "Ribonucleotide reductase M1 and M2 (RR-M1, -M2), cytidine deaminase (CDA), deoxycytidine deaminase (dCDA), deoxycytidine kinase (dCK), and excision repair cross complementation—1 (ERCC-1) expression in advanced malignancies treated with combined oxaliplatin and gemcitabine," Proc ASCO 22:3456.

Machover et al. (1996) "Two consecutive phase II studies of oxaliplatin (L-OHP) for treatment of patients with advanced colorectal carcinoma who were resistant to previous treatment with fluoropyrimidines" Ann. Oncol. 7(1):95-98.

Metzger et al. (1996) "ERCC1 expression correlates with response of primary gastric cancer to cisplatin-based chemotherapy," Proc AACR 37:A1350.

Metzger et al. (1996) "Excision repair cross complementing (ERCC)-1 gene in primary gastric cancer: A determinant of response to cisplatin-based chemotherapy," Proc ASCO 15:A505.

Metzger et al. (1998) "ERCC1 mRNA levels complement thymidylate synthase mRNA levels in predicting response and survival for gastric cancer patients receiving combination cisplatin and 5-fluorouracil chemotherapy," J Clin Oncol 16:309-316.

Moertel (1994) "Chemotherapy for colorectal cancer" N. Engl. J. Med. 330:1136-1142.

Park et al. (2002) "ERCC1 polymorphism is associated with differential ERCC1 mRNA levels," Proc AACR 43:1591.

Park et al. (2003) "ERCC1 gene polymorphism as a predictor for clinical outcome in advanced colorectal cancer patients treated with platinum-based chemotherapy," Clinical Advances in Hematology and Oncology 1(3):162-166.

Shibata et al. (1998) "RT-PCR analysis of thymidylate synthetase (TS), ribonucleotide reductase (RR), and ERCC-1 expression in patients (PTS) with locally advanced gastrointestinal (GI) malignancies treated with surgery, intraoperative radiation therapy (IORT) with concurrent 5-FU and external beam radiation (EBRT) with prolonged 5-FU infusion," Proc ASCO 17:562a.

Shirota et al. (2001) "ERCC1 and TS expression levels predict survival in patients with advanced colorectal carcinoma under 5-FU/oxaliplatin treatment," Proc ASCO 20:513.

Stoehlmacher et al. (2002) "The predictive value of thymidylate synthase (TS) and excision repair cross-complementing (ERCC) gene in first- and second-line chemotherapy of patients with colorectal cancer," Amer J Oncol Rev 1:29-32.

Stoehlmacher et al. (2003) "Pharmacogenetic aspects in treatment of colorectal cancer—an update" Pharmacogenomics 4(6):767-777.

Viguier et al. (2005) "ERCC1 codon 118 polymorphism is a predictive factor for the tumor response to oxaliplatin/5-fluorouracil combination chemotherapy in patients with advanced colorectal cancer" Clin. Cancer Res. 11:6212-6217.

Waters and Cunningham (2001) "The changing face of chemotherapy in colorectal cancer" Br. J. Cancer 84(1):1-7.

Yacoub et al. (2003) "Epidermal Growth Factor and Ionizing Radiation Up-regulate the DNA Repair Genes XRCC1 and ERCC1 in DU145 and LNCaP Prostate Carcinoma through MAPK Signaling" Radiation Res. 159:439-452.

Yun et al. (2003) "Association of genetic polymorphisms of IL-8 and its receptor CXCR1 and survival of patients with metastatic colorectal cancer treated with 5FU/oxaliplatin" Proc ASCO 22:847.

Chang et al. (2008) "ERCC1 codon 118 C→T polymorphism associated with ERCC1 expression and outcome of FOLFOX-4 treatment in Asian patients with metastatic colorectal carcinoma" Cancer Sci. 100(2):278-283.

Huang et al. (2008) "ERCC1 polymorphism, expression and clinical outcome of oxaliplatin-based adjuvant chemotherapy in gastric cancer" World J. Gastroenterol. 14(41):6401-6407.

Isla et al. (2004) "Single nucleotide polymorphisms and outcome in docetaxel—cisplatin-treated advanced non-small-cell lung cancer" Annals of Oncology 15:1194-1203.

Kamikozuru et al. (2008) "ERCC1 codon 118 polymorphism is a useful prognostic marker in patients with pancreatic cancer treated with platinum-based chemotherapy" International Journal of Oncology 32:1091-1096.

Kang et al. (2006) "Association between excision repair cross-complementation group 1 polymorphism and clinical outcome of platinum-based chemotherapy in patients with epithelial ovarian cancer" Experimental and Molecular Medicine 38(3):320-324.

Keam et al. (2008) "Modified FOLFOX-6 chemotherapy in advanced gastric cancer: Results of phase II study and comprehensive analysis of polymorphisms as a predictive and prognostic marker" BMC Cancer 8:148, 10 pgs.

Krivak et al. (2008) "Relationship Between ERCC1 Polymorphisms, Disease Progression, and Survival in Gynecologic Oncology Group Phase III Trial of Intraperitoneal Versus Intravenous Cisplatin and Paclitaxel for Stage III Epithelial Ovarian Cancer" J. Clin. Oncol. 26(21):3598-3606.

Liu et al. (2005) "Impact of Gene Polymorphisms on Clinical Outcome for Stage IV Melanoma Patients Treated with Biochemotherapy: An Exploratory Study" Clin. Cancer Res. 11:1237-1246.

Martinez-Balibrea et al. (2008) "Pharmacogenetic approach for capecitabine or 5-fluorouracil selection to be combined with oxaliplatin as first-line chemotherapy in advanced colorectal cancer" European J. of Cancer 44:1229-1237.

Pare et al. (2008) "Pharmacogenetic prediction of clinical outcome in advanced colorectal cancer patients receiving oxaliplatin/5-fluorouracil as first-line chemotherapy" British J. Cancer 99:1050-1055.

Park et al. (2006) "Effect of ERCC1 Polymorphisms and Modification by Smoking on the Survival of Non-Small Cell Lung Cancer Patients" Medical Oncology 23(4):489-498.

Ruzzo et al. (2007) "Pharmacogenetic Profiling in Patients with Advanced Colorectal Cancer treated with First-Line FOLFOX-4 Chemotherapy" J. Clin. Oncol. 25(10):1247-1254.

Ryu et al. (2004) "Association between polymorphism of ERCC1 and XPD and Survival in non-small-cell lung cancer patients treated with cisplatin combination chemotherapy" Lung Cancer 44:311-316.

Smith et al. (2007) "ERCC1 Genotype and Phenotype in Epithelial Ovarian Cancer Identify Patients Likely to Benefit from Paclitazel Treatment in Addition to Platinum-Based Therapy" J. Clin. Oncol. 25(33):5172-5179.

Steffensen et al. (2008) "Prediction of response to chemotherapy by ERCC1 immunohistochemistry and ERCC1 polymorphism in ovarian cancer" Int. J. Gynecol. Cancer 18:702-710.

Stoehlmacher et al. (2004) "A multivariate analysis of genomic polymorphisms: prediction of clinical outcome to 5-FU/oxaliplatin combination chemotherapy in refractory colorectal cancer" British J. Cancer 91:344-354.

Suk et al. (2005) "Polymorphisms in ERCC1 and Grade 2 or 4 Toxicity in Non-Small Cell Lung Cancer Patients" Clin. Cancer Res. 11:1534-1538.

Tibaldi et al. (2008) "Correlation of CDA, ERCC1, and XPD polymorphisms with Response and Survival in Gemcitabine/Cisplatin—Treated Advanced Non-Small Cell Lung Cancer Patients" Clin. Cancer Res. 14(6):1797-1803.

Zhou et al. (2004) "Excision Repair Cross-Complementation Group 1 Polymorphism Predicts Overall Survival in Advanced Non-Small Cell Lung Cancer Patients Treated With Platinum-Based Chemotherapy" Clin. Cancer Res. 10:4939-4943.

Matsubara et al. (2008) "Impacts of excision repair cross-complementing gene 1 (ERCC1), dihydropyrirnidine dehydrogenase, and epidermal growth factor receptor on the outcomes of patients with advanced gastric cancer," *British Journal of Cancer* 98:832-839.

Takenaka et al. (2007) "Combined evaluation of Rad51 and ERCC1 expressions for sensitivity to platinum agents in non-small cell lung cancer," *Int. J. Cancer* 121:895-900.

U.S. Appl. No. 11/173,889—Non-Final Office Action dated Jun. 10, 2009.

U.S. Appl. No. 11/173,889—Non-Final Office Action dated May 23, 2008.

U.S. Appl. No. 11/173,889—Restriction Requirement dated Oct. 1, 2007.

* cited by examiner

| Parameter | Cut-point | Normal Tissue | | | | | Cut-point | Tumor Tissue | | | | |
|---|---|---|---|---|---|---|---|---|---|---|---|---|
| | | n | Probability of 5-yr recurrence | Relative Risk | | $P^a$ | | n | Probability of 5-yr recurrence | Relative Risk | | $P^a$ |
| | | | | Risk | 95% CI | | | | | Risk | 95% CI | |
| TS | ≤2.8 | 40 | 0.44 ± 0.11 | 1.00 | Reference | <0.01 | ≤2.8 | 43 | 0.53 ± 0.11 | 1.00 | Reference | 0.51 |
| | >2.8 | 8 | 0.75[b] ± 0.15 | 5.44 | 1.85-16.01 | | >2.8 | 14 | 0.68 ± 0.14 | 1.98 | 0.90-4.35 | |
| DPD | ≤1.2 | 30 | 0.38 ± 0.12 | 1.00 | Reference | 0.04 | ≤0.3 | 7 | 0.38 ± 0.21 | 1.00 | Reference | 0.94 |
| | >1.2 | 13 | 0.88 ± 0.11 | 3.11 | 1.19-8.13 | | >0.3 | 44 | 0.54 ± 0.09 | 1.24 | 0.29-5.31 | |
| ERCC-1 | ≤2.2 | 40 | 0.47 ± 0.11 | 1.00 | Reference | 0.03 | ≤0.7 | 8 | 0.75 ± 0.15 | 1.00 | Reference | 0.14 |
| | >2.2 | 9 | 0.81 ± 0.16 | 3.44 | 1.32-8.93 | | >0.7 | 48 | 0.50 ± 0.10 | 0.41 | 0.16-1.03 | |
| | ≤1.4 | 29 | 0.45 ± 0.12 | 1.00 | Reference | 0.26 | ≤2.8 | 46 | 0.54 ± 0.10 | 1.00 | Reference | 0.56 |
| | >1.4 | 16 | 0.60 ± 0.18 | 1.61 | 0.63-4.09 | | >2.8 | 7 | 0.71 ± 0.22 | 1.74 | 0.65-4.68 | |
| VEGF | ≤2.9 | 36 | 0.39 ± 0.11 | 1.00 | Reference | 0.05 | ≤7.2 | 38 | 0.32 ± 0.09 | 1.00 | Reference | 0.03 |
| | >2.9 | 10 | 0.85 ± 0.14 | 2.76 | 1.08-7.03 | | >7.2 | 18 | 0.91 ± 0.08 | 3.23 | 1.50-6.97 | | a. Based on log-rank test statistics for cut points, but after 2,000 bootstrap-like simulations to adjust for selection of optimal cut point; P values remained similar when metastasis as an event (local occurrence).
b. Probability at 4 years

Figure 1

POLYMORPHISMS IN THE ERCC1 GENE FOR PREDICTING TREATMENT OUTCOME

CROSS-REFERENCE TO RELATED APPLICATIONS

This application claims priority under 35 U.S.C. §119(e) to the following U.S. Provisional Application Nos. 60/400,249; 60/400,250; 60/400,253; and 60/400,276, each filed on the same day of Jul. 31, 2002. The contents of these applications are hereby incorporated by reference into the present disclosure.

FIELD OF THE INVENTION

This invention relates to the field of pharmacogenomics and specifically to the application of genetic polymorphism to diagnosing and treating diseases.

BACKGROUND OF THE INVENTION

In nature, organisms of the same species usually differ from each other in some aspects, e.g., their appearance. The differences are genetically determined and are referred to as polymorphism. At many gene loci, two or more alleles may occur (genetic polymorphism). Genetic polymorphism is defined as the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism may play a role in determining individual differences in the response to drugs. Cancer chemotherapy is limited by the predisposition of specific populations to drug toxicity or poor drug response. Thus, for example, pharmacogenetics (the effect of genetic differences on drug response) has been applied in cancer chemotherapy to understand the significant inter-individual variations in responses and toxicities to the administration of anti-cancer drugs, which may be due to genetic alterations in drug metabolizing enzymes or receptor expression. See co-pending U.S. application Ser. No. 09/715,764, incorporated by reference herein.

Polymorphism is also associated with cancer susceptibility (oncogenes, tumor suppressor genes and genes of enzymes involved in metabolic pathways) of individuals. In patients younger than 35 years, several markers of increased cancer risk have been identified. For example, prostate specific antigen (PSA) can be used for the early detection of prostate cancer in asymptomatic younger males, while particular cytochrome P4501A1 and gluthathione S-transferase M1 genotypes influence the risk of developing prostate cancer in younger patients. Similarly, mutations in the tumor suppressor gene, p53, are associated with brain tumors in young adults.

Thus a need exists to identify genetic markers that are predictive of drug toxicity or poor drug response. This invention satisfies this need and provides related advantages as well.

DESCRIPTION OF THE EMBODIMENTS

In one embodiment, the invention comprises the use of the allelic variant of the polymorphic region of the gene of interest to select a cancer treatment protocol. These methods of use include prognostic, diagnostic, and therapeutic methods. In one aspect, the variant of interest is expressed as a gene that is highly expressed (based on mRNA expression levels) of the gene in the adjacent and corresponding "normal" tissue remaining after surgical resection. In another aspect, the variant of interest is detected at the genomic level and can comprise regions of the gene which are, or are not, ultimately transcribed and translated into protein. For example, such regions include, but are not limited to the untranslated promoter regions or the untranslated 3' region of the gene.

Methods to detect polymorphisms include using nucleic acids encompassing the polymorphic region as probes or primers to determine whether a subject has or is at risk of developing cancer and/or the subject's response to chemotherapy. Alternatively, mRNA levels can be detected using nucleic acid probes or arrays.

In one aspect, the cancer comprises a cancer or neoplasm that is "treatable" by use of platinum therapy, e.g., oxaliplatin or cisplatin or 5-flurouridine (5-FU) and the orally available FU therapy, sold under the name Xeloda (Roche). Non-limiting examples of such cancers include, but are not limited to rectal cancer, colorectal cancer, colon cancer, gastric cancer, lung cancer, esophageal cancers. In one aspect, the sample to be tested is the actual tumor tissue. In another aspect, the sample to be tested in the method is normal "corresponding" tissue to the tumor tissue, e.g., normal lung tissue is considered to be the corresponding normal tissue to lung cancer tissue. In yet a further example, the sample is any tissue of the patient, and can include peripheral blood lymphocytes.

In another embodiment, the invention provides a kit for amplifying and/or for determining the molecular structure of at least a portion of the gene of interest, comprising a probe or primer capable of hybridizing to the gene of interest and instructions for use. In one embodiment, the probe or primer is capable of hybridizing to an allelic variant of the gene of interest.

Other features and advantages of the invention will be apparent from the following detailed description and claims.

BRIEF DESCRIPTION OF THE FIGURES

FIG. 1 shows time to local recurrence in rectal cancer based on molecular parameters.

MODES FOR CARRYING OUT THE INVENTION

Figure 2A:
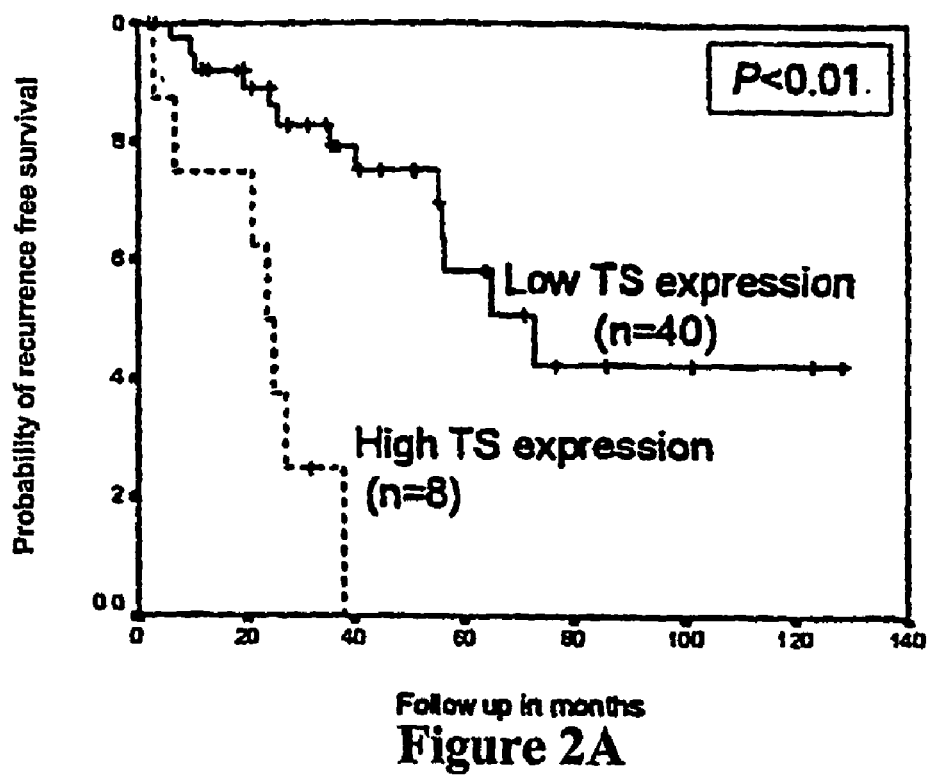
FIGS. 2A through 2D show the estimated probability of recurrence free survival in patients with rectal cancer versus gene expressions of TS, DPD, ERCC1, and VEGF in normal rectal tissue. See Experimental Number 1 for experimental details.
Figure 2B:
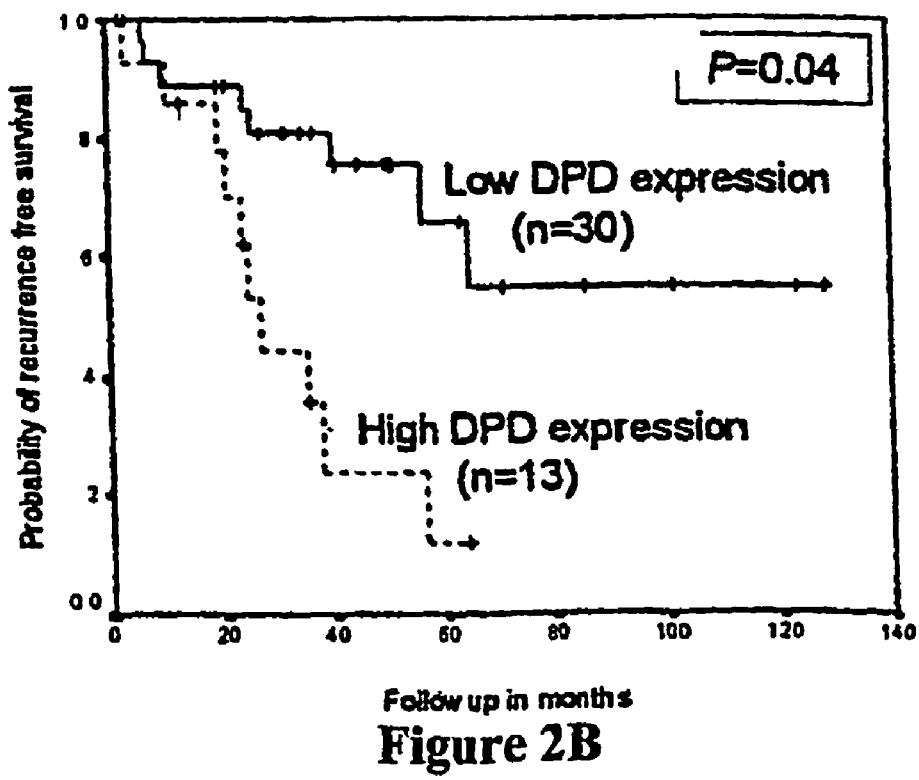
Figure 2C:
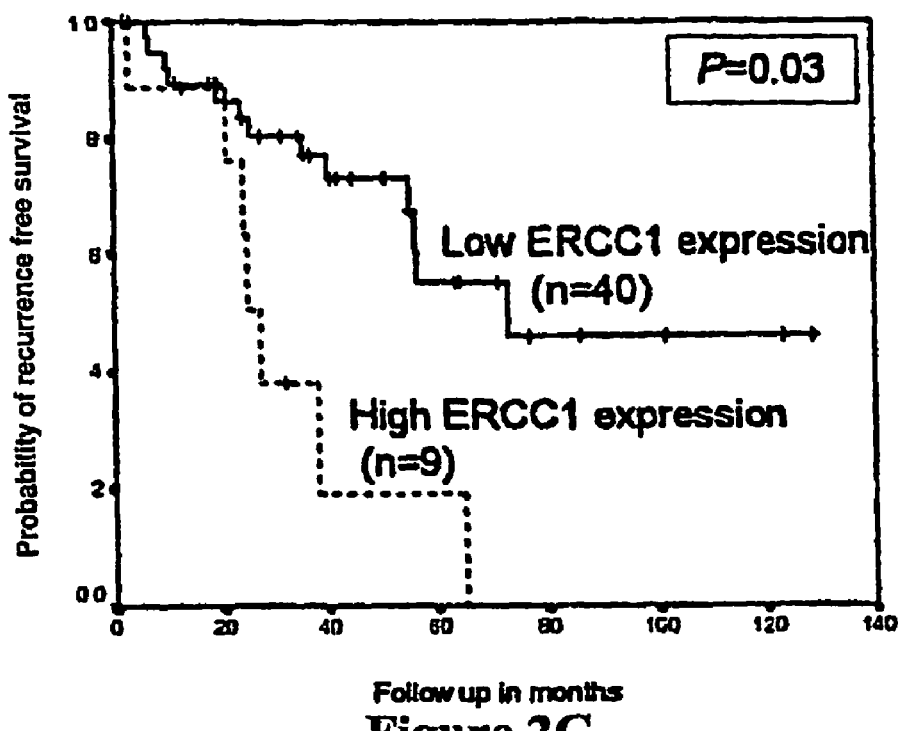
Figure 2D:
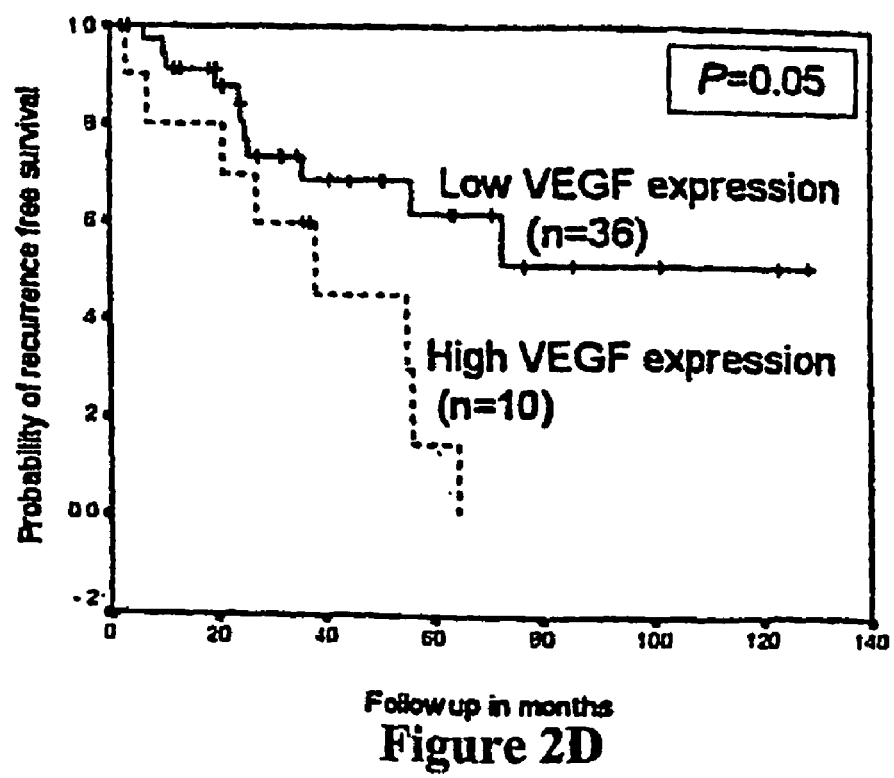
Figure 3:
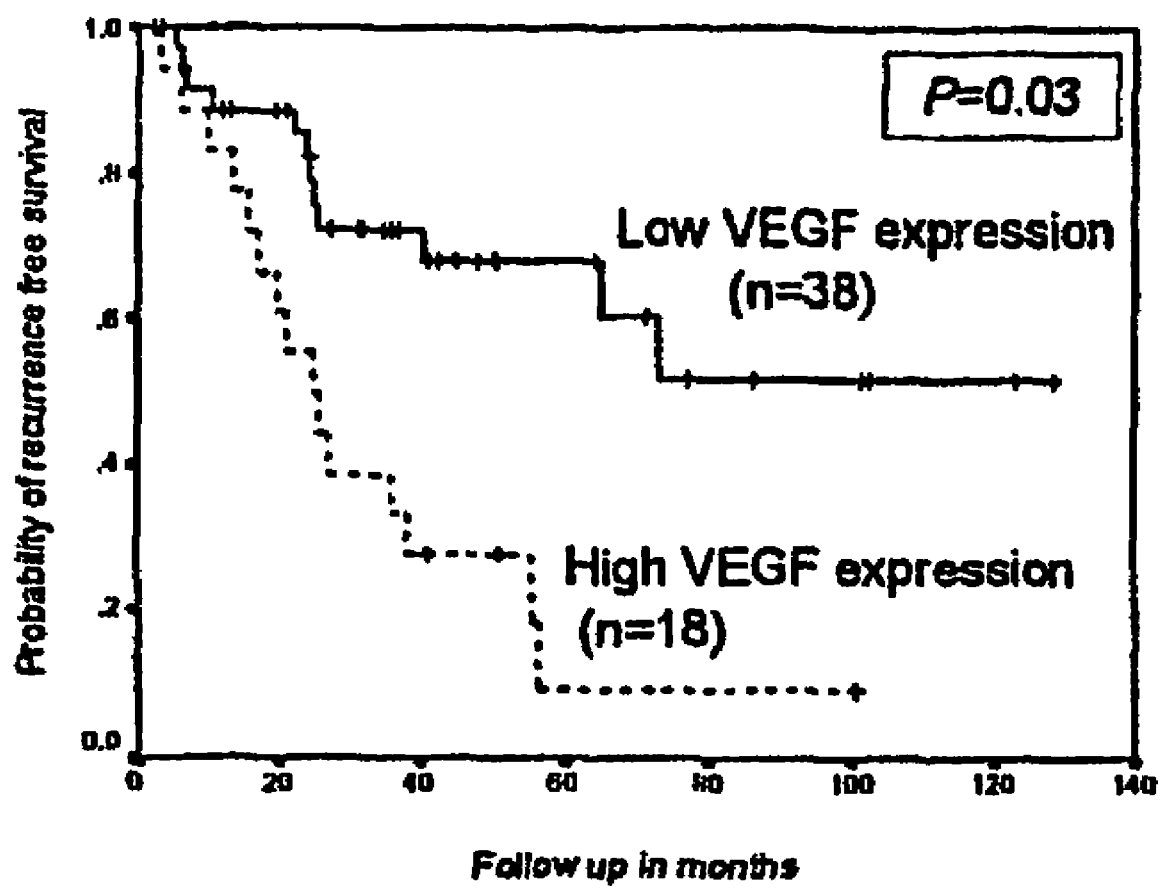
FIG. 3 shows the estimated probability of recurrence free survival in patients with rectal cancer versus gene expression of VEGF in rectal cancer tissue. See Experimental Number 1 for experimental details.

The present invention provides methods and kits to determine a subject risk of cancer and response to cancer treatment by determining the subject's genotype at the gene of interest. Other aspects of the invention are described below or will be apparent to one of skill in the art in light of the present disclosure.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, eg., Sambrook et al. MOLECULAR CLONING: A LABORATORY MANUAL, $2^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc., N.Y.); PCR: A PRACTICAL APPROACH (M. MacPherson et al. IRL Press at Oxford University Press (1991)); PCR 2: A PRACTICAL APPROACH (M J. MacPherson, B. D. Hames and G. R. Taylor eds. (1995)); ANTIBODIES, A LABORATORY MANUAL (Harlow and Lane eds. (1988)); ANIMAL CELL CULTURE (R. I. Freshney ed. (1987)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); IMMUNOCHEMICAL METHODS IN CELL AND MOLECULAR BIOLOGY (Mayer and Walker, eds., Academic Press, London (1987)); HANDBOOK OF EXPERIMENTAL IMMUNOLOGY, Volumes I-IV (D. M. Weir and C. C. Blackwell, eds. (1986)); MANIPULATING THE MOUSE EMBRYO (Cold Spring Harbor Laboratory Press, Cold Spring Harbor, N.Y. (1986)).

DEFINITIONS

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of the gene of interest" refers to a region of the gene of interest having one of a plurality of nucleotide sequences found in that region of the gene in other individuals. "Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x. The nucleotide sequences and complementary sequences thereof are always given in the 5' to 3' direction. The term "complement" and "reverse complement" are used interchangeably herein.

A "non-human animal" of the invention can include mammals such as rodents, non-human primates, sheep, goats, horses, dogs, cows, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

This invention provides a method for selecting a therapeutic regimen or determining if a certain therapeutic regimen is more likely to treat a cancer or is the appropriate chemotherapy for that patient than other chemotherapies that may be available to the patient. In general, a therapy is considered to "treat" cancer if it provides one or more of the following treatment outcomes: reduce or delay recurrence of the cancer after the initial therapy; increase median survival time or decrease metastases. The method is particularly suited to determining which patients will be responsive or experience a positive treatment outcome to a chemotherapeutic regimen involving administration of a fluropyrimidine drug such as 5-FU or a platinum drug such as oxaliplatin or cisplatin. In one embodiment, the chemotherapeutic regimen further comprises radiation therapy.

The method comprises isolating a suitable cell or tissue sample from the patient and screening for a genomic polymorphism or genotype that has been correlated by the Applicants to treatment outcome of the cancer. In one aspect, the cancer is a cancer that can be treated by the administration of a chemotherapeutic drug selected from the group consisting of fluoropyrimidine or a platinum drug. In another aspect, the cancer is selected from the group consisting of esophageal cancer, gastric cancer, colon cancer, rectal cancer, colorectal cancer and lung cancer.

In one aspect, the polymorphism is present in a "silent" region of the gene, in another it is in the promoter region and in yet another it is in the 3' untranslated region. In yet a further embodiment, the polymorphism increases expression at the mRNA level.

In one embodiment, the suitable tissue or cell sample comprises normal tissue adjacent to the site of tumor biopsy or resection. For example, one would select normal rectal tissue adjacent to the site of rectal cancer tumor removal. As used herein, "adjacent" mean about 0.5 mm, or about 1.0 mm, or about 1.5 mm, or about 2.0 mm or about 2.5 mm, or about 3.0 mm, or about 3.5 mm, or about 4.0 mm or about 4.5 mm or about 5.0 mm or alternatively any distance the only limitation being that the normal tissue be of the same type as the tumor or neoplasm.

In another embodiment, the tissue is the tumor tissue itself. In yet a further embodiment, any cell expected to carry the gene of interest, when the polymorphism is, for example, genetic, such as a peripheral blood lymphocyte isolated from the patient, is a suitable cell or tissue sample.

Genetic polymorphisms that can be predictive of outcome include, but are not limited to polymorphisms occurring in a gene selected from the group consisting of thymidylate synthase gene, excision repair complementation group gene (ERCC1), VEGF, ERC2 gene, XRCC-1 gene, human glutathione s-transferase P1 gene, epidermal growth factor receptor gene, matrix metalloproteinase genes (−1, and −3), interleukin 8 (IL-8) gene, D-pyrimidine dehydrogenase (DPD) and CXC chemokine.

This invention also provides a method for reducing chemically induced neurotoxicity associated with cancer chemotherapy in a patient comprising administering to the patient an effective amount of a COX-2 inhibitor or its equivalent to a patient in need thereof In one embodiment, the neurotoxicity is the result of administration of chemotherapy comprising oxaliplatin, cisplatin or a fluoropyrimidine such as 5-FU or Xeloda.

A method for determining if a human patient is more likely to experience tumor recurrence after surgical removal of said tumor, comprising determining the expression level of a gene selected from the group consisting of TS, D-pyrimidine dehydrogenase (DPD), ERCC1 and VEGF, in a cell or sample isolated from normal tissue adjacent to said tumor and correlating said expression level with normal levels, wherein overexpression of said gene is predictive to identify patients at risk for tumor recurrence. In one aspect, the tumor is associated with rectal cancer.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi, S. and Kramer, F. R. (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis, L. G. (1998) Science 279:1228-9) as has the use of multiple beacons simultaneously (Marras, S. A. (1999) Genet. Anal. 14:151-6). A quenching molecule is useful with a particular fluorophore if it has sufficient spectral overlap to substantially inhibit fluorescence of the fluorophore when the two are held proixmal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88: 7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the poymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

The term "treating" as used herein is intended to encompass curing as well as ameliorating at least one symptom of the condition or disease. For example, in the case of cancer, treatment includes a reduction in cachexia. Evidence of treatment may be clinical or subclinical.

As used herein, the term "vector" refers to a nucleic acid molecule capable of transporting another nucleic acid to which it has been linked. One type of preferred vector is an episome, ie., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Nucleic Acids

In one aspect, the nucleic acid sequences of the gene's allelic variants, or portions thereof, can be the basis for probes or primers, e.g., in methods for determining the identity of the allelic variant of the polymorphic region. Thus, they can be used in the methods of the invention to determine whether a subject is at risk of developing colorectal cancer.

The methods of the invention can use nucleic acids isolated from vertebrates. In one aspect, the vertebrate nucleic acids are mammalian nucleic acids. In a further aspect, the nucleic acids used in the methods of the invention are a human nucleic acids. Primers for use in the methods of the invention are nucleic acids which hybridize to a nucleic acid sequence which is adjacent to the region of interest (e.g. the 5'-untranslated region of the TS gene) or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the gene of interest, and which by hybridization or absence of hybridization to the DNA of a subject will be indicative of the identity of the allelic variant of the polymorphic region of the gene of interest.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the gene of interest. Thus, such primers can be specific for the gene of interest sequence, so long as they have a nucleotide sequence which is capable of hybridizing to the gene of interest.

The probe or primer may further comprises a label attached thereto, which, e.g., is capable of being detected, e.g. the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564; and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane (see, e.g., Letsinger et al., (1989) Proc. Natl. Acad. Sci. U.S.A. 86:6553-6556; Lemaitre et al., (1987) Proc. Natl. Acad. Sci. 84:648-652; and PCT Publication No. WO 88/09810, published Dec. 15, 1988), hybridization-triggered cleavage agents, (see, e.g., Krol et al., (1988) BioTechniques 6:958-976) or intercalating agents (see, e.g., Zon (1988) Pharm. Res. 5:539-549). To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof to be used in the methods of the invention can be prepared according to methods well known in the art and described, e.g., in Sambrook et al. (1989) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions.

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports (Sarin et al., (1988) Proc. Natl. Acad. Sci. U.S.A. 85:7448-7451), etc.

Predictive Medicine and Pharmacogenomics

The invention further features predictive medicines, which are based, at least in part, on determination of the identity of the polymorphic region of the gene of interest.

For example, information obtained using the diagnostic assays described herein is useful for determining if a subject will respond to cancer treatment of a given type. Based on the prognostic information, a doctor can recommend a regimen (e.g. diet or exercise) or therapeutic protocol, useful for treating cancer in the individual.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; and 2) to better determine the appropriate dosage of a particular drug. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Detection of point mutations can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al., (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert ((1997) Proc. Natl Acad Sci USA 74:560) or Sanger (Sanger et al. (1977) Proc. Nat. Acad. Sci 74:5463). It is also contemplated that any of a variety of automated sequencing procedures can be utilized when performing the subject assays (Biotechniques (1995) 19:448), including sequencing by mass spectrometry (see, for example, U.S. Pat. No. 5,547,835 and international patent application Publication Number WO94/16101, entitled DNA Sequencing by Mass Spectrometry by H. Koster; U.S. Pat. No. 5,547,835 and international patent application Publication Number WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl Biochem Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method Of DNA Sequencing Employing A Mixed DNA-Polymer Chain Probe" and U.S. Pat. No. 5,571,676 entitled "Method For Mismatch-Directed In Vitro DNA Sequencing".

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility is used to identify the particular allelic variant. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saild et al. (1986) Nature 324:163); Saiki et al. (1989) Proc. Natl Acad. Sci USA 86:6230; and Wallace et al. (1979) Nucl. Acids Res. 6:3543). Such allele specific oligonucleotide hybridization techniques may be used for the detection of the nucleotide changes in the polylmorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238; Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell Probes 6:1).

In another embodiment, identification of the allelic variant is carried out using an oligonucleotide ligation assay (OLA), as described, e.g., in U.S. Pat. No. 4,998,617 and in Landegren, U. et al. Science 241:1077-1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. (1996)Nucleic Acids Res. 24: 3728), OLA combined with PCR permits typing of two alleles in a single microtiter well. By marling each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen, D. et al. (French Patent 2,650, 840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al. (1989) Nucl. Acids. Res. 17:7779-7784; Sokolov, B. P. (1990) Nucl. Acids Res. 18:3671; Syvanen, A.-C., et al. (1990) Genomics 8:684-692; Kuppuswamy, M. N. et al. (1991) Proc. Natl. Acad. Sci. (U.S.A.) 88:1143-1147; Prezant, T. R. et al. (1992) Hum. Mutat. 1:159-164; Ugozzoli, L. et al. (1992) GATA 9:107-112; Nyren, P. et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

Antibodies directed against wild type or mutant peptides encoded by the allelic variants of the gene of interest may also be used in disease diagnostics and prognostics. Such diagnostic methods, may be used to detect abnormalities in the level of expression of the peptide, or abnormalities in the structure and/or tissue, cellular, or subcellular location of the peptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al., (1989) supra, at Chapter 18. The protein detection and isolation methods employed herein can also be such as those described in Harlow and Lane, (1988) supra. This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of the peptides or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing colorectal cancer.

Sample nucleic acid for use in the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo, G. J. (1992) "PCR In Situ Hybridization: Protocols And Applications", Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

Methods of Treatment

The invention further provides methods of treating subjects having cancer. In one embodiment, the method comprises (a) determining the identity of the allelic variant; and (b) administering to the subject an effective amount of a compound that provides therapeutic benefits for the specific allelic variant.

Kits

As set forth herein, the invention provides methods, e.g., diagnostic and therapeutic methods, e.g., for determining the type of allelic variant of a polymorphic region present in the gene of interest, such as a human TS gene. In some embodiments, the methods use probes or primers comprising nucleotide sequences which are complementary to the polymorphic region of the gene of interest. Accordingly, the invention provides kits for performing these methods.

In an embodiment, the invention provides a kit for determining whether a subject responds to cancer treatment or alternatively one of various treatment options. The kist contain one of more of the compositions described above and instructions for use. As an example only, the invention also provides kits for determining response to cancer treatment containing a first and a second oligonucleotide specific for the polymorphic region of the TS gene, namely in the 5'-untranslated region. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard, T. (1986) "An Introduction to Radioimmunoassay and Related Techniques" Elsevier Science Publishers, Amsterdam, The Netherlands ; Bullock, G. R. et al., "Techniques in Immunocytochemistry" Academic Press, Orlando, Fla. Vol. 1 (1982), Vol. 2 (1983), Vol. 3 (1985); Tijssen, P., (1985) "Practice and Theory of Immunoassays: Laboratory Techniques in Biochemistry and Molecular Biology", Elsevier Science Publishers, Amsterdam, The Netherlands.

The test samples used in the diagnostic kits include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the gene of interest.

As amenable, these suggested kit components maybe packaged in a manner customary for use by those of skill in the art. For example, these suggested kit components may be provided in solution or as a liquid dispersion or the like.

OTHER USES FOR THE NUCLEIC ACIDS OF THE INVENTION

The identification of the allele of the gene of interest can also be useful for identifying an individual among other individuals from the same species. For example, DNA sequences can be used as a fingerprint for detection of different individuals within the same species (Thompson, J. S. and Thompson, eds., (1991) "Genetics in Medicine", W B Saunders Co., Philadelphia, Pa.). This is useful, e.g., in forensic studies.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook, et al., (1989)

The invention now being generally described, it will be more readily understood by reference to the following examples which are included merely for purposes of illustration of certain aspects and embodiments of the present invention, and are not intended to limit the invention.

EXAMPLES

Example 1

Gene Expression Profile in Normal Tissue Predicts Pelvic Recurrence in Patients with Rectal Cancer Treated with Adjuvant Chemoradiation Therapy The incidence of colorectal cancer has been rising within the last decade and is now as high as 41,000 estimated new cases and 8,500 deaths in the USA per year. (Jemal A. et al. (2002) CA Cancer J Clin 52:23-47). In stage II-IV rectal cancer, local recurrence occurs in 20-70% of patients treated with surgery alone. (Kapiteijn E. et al. (2001) N. Engl. J. Med. 345:638-646). Adjuvant radio-chemotherapy has been generally accepted in the United States as standard therapy for patients who had surgical resection for high-risk rectal cancer. (NIH Consensus Conference. Adjuvant Therapy For Patients With Colon And Rectal Cancer (1990) JAMA 264: 1444-1450).

Previous studies in rectal cancer showed associations between elevated levels of certain genes, including TS and DPD. (Salonga D. et al. (2000) Clin. Cancer Res. 6:1322-

1327 and Ishikawa et al. (1999) Clin. Cancer Res. 5:883-889) and a worse outcome after neoadjuvant treatment with 5-FU.

Thus, it would be useful to identify a maker that would predict pelvic recurrence in patients with rectal cancer treated with adjuvant chemo-radiation. To this end, mRNA levels of 5 putative response determinant genes in tumor plus adjacent normal tissues were measured. The investigated genes were involved in the 5-FU pathway (TS, DPD), in DNA repair (ERCC1, RAD51), and angiogenesis (VEGF).

Methods: Seventy-three (73) patients with locally advanced rectal cancer (UICC stage II and III) were selected. They had been previously treated with adjuvant pelvic irradiation (45 Gy) to the whole pelvis with an additional boost up to 54 Gy plus 5-FU infusion therapy following tumor resection tissue acquisition during surgery. QRT-PCR (a fluorescence-based, quantitative real-time detection method (Taqman®)) was performed on RNA extracted from formalin-fixed, paraffin-embedded, laser-capture-microdissected tissue to establish gene expression levels. The mRNA was reverse transcribed to cDNA and the genes of interest were quantified as well as an internal reference gene ($\beta$-Actin) as a control. All gene expression levels were log-transformed prior to analysis. The maximal $c^2$ method of Miller, Siegmund (Miller R. and Siegmund D. Biometrics (1982) 38:1011-1016) and Halpem (Halpem J. (1982) Biometrics 38:1017-1023) was used to determine which gene expression best segregated patients into poor- and good-prognosis subgroups 2000 bootstrap-like simulations were used to estimate the distribution of the maximal $c^2$ statistics under the null hypothesis of no association.

Results: Intra-tumoral mRNA levels of genes associated with the 5-FU metabolism and DNA repair were not associated with the outcome after adjuvant radio-chemotherapy in patients with rectal cancer. Gene expression levels of TS, DPD, ERCC1, and VEGF in the tumor adjacent normal tissue were associated with the clinical outcome and can be useful to identify patients at higher risk for pelvic recurrence. These results show that the gene expression of the tumor adjacent normal tissue but not of the tumor tissue is representative for the biological behavior of the tumor cells, remaining after surgery, that may cause local tumor recurrence.

Example 2

TS Polymorphism in the Promoter Region Predicts Pelvic Recurrence in Treated Cancer Patients The enzyme thymidylate synthase (TS) catalyzes the intracellular conversion of deoxyuridylate to deoxythymidylate which is the sole de novo source of thymidylate, an essential precursor for DNA synthesis. (Heidelberger C. et al. (1957) Nature (179):663-666). It has been shown that the human thymidylate synthase gene (hTS) is polymorphic with either double or triple tandem repeats of a 28 base-pair sequence downstream of the cap-site in the 5' terminal regulatory region. (Horie N. et al. (1995) Cell Struct. Funct. 20:191-197).

A polymorphism in the TS gene and its correlation with the efficacy of treatment with 5-FU was previously described in co-owned U.S. patent application Ser. No. 09/715,764, (the entire contents of which are incorporated by reference

TABLE 1

Time to local recurrence in rectal cancer based on demographic and clinical parameters

| Parameter | n | Probability ± SE of 5-yr recurrence | Median time to recurrence | | Relative Risk | | $P^a$ |
|---|---|---|---|---|---|---|---|
| | | | Month | 95% CI | Risk | 95% CI | |
| Total Patients | 73 | 0.53 ± 0.08 | 57.0 | 38.4, 130.2+[b] | | | |
| Age | | | | | | | |
| <50 years | 30 | 0.48 ± 0.11 | 65.7 | 27.3, 130.2+ | 1.00 | Reference | |
| ≧50 years | 43 | 0.57 ± 0.11 | 56.0 | 25.8, 124.6+ | 1.24 | 0.60-2.56 | 0.56 |
| Sex | | | | | | | |
| Male | 48 | 0.58 ± 0.10 | 56.0 | 27.3, 124.6+ | 1.00 | Reference | |
| Female | 25 | 0.44 ± 0.13 | 130.2+ | 36.0, 130.2+ | 0.62 | 0.28-1.40 | 0.24 |
| Race | | | | | | | |
| Caucasian | 50 | 0.57 ± 0.09 | 56.0 | 25.4, 124.6+ | 1.00 | Reference | |
| Other | 23 | 0.43 ± 0.14 | 65.7 | 40.5, 130.2+ | 0.63 | 0.28-1.40 | 0.25 |
| pT | | | | | | | |
| $pT_2$ | 22 | 0.61 ± 0.14 | 56.0 | 25.8, 130.2+ | 1.00 | Reference | |
| $pT_3$ | 51 | 0.48 ± 0.09 | 65.7 | 38.4, 102.7+ | 0.96 | 0.45-2.04 | 0.91 |
| pN | | | | | | | |
| $pN_0$ | 35 | 0.43 ± 0.11 | 65.7 | 40.5, 130.2+ | 1.00 | Reference | |
| $PN_+$ | 38 | 0.60 ± 0.10 | 56.0 | 25.8, 124.6+ | 1.31 | 0.64-2.67 | 0.46 |
| Grade | | | | | | | |
| I-II | 57 | 0.60 ± 0.09 | 56.0 | 27.3, 130.2+ | 1.00 | Reference | |
| III | 16 | 0.24 ± 0.12 | 103.7+ | 65.7, 103.7+ | 0.56 | 0.19-1.59 | 0.26 |
| Surgery Type | | | | | | | |
| $APR^c$ | 20 | 0.73 ± 0.15 | 56.0 | 25.2, 130.2+ | 1.00 | Reference | |
| LAR | 44 | 0.48 ± 0.09 | 65.7 | 38.4, 102.7+ | 0.82 | 0.37-1.80 | 0.66 |
| TRA | 9 | 0.22 ± 0.14 | 103.7+ | 103.7+, 103.7+ | 0.51 | 0.11-2.35 | |

[a]Based on Log-rank test.
[b]The estimates were not reached.
[c]APR, abdominal perineal resection; LAR, lower anterior resection; TRA, transanal resection herein.) The predictive polymorphism reported in this disclosure is a tandemly repeated 28 base pair sequence in the thymidilate synthase gene's 5' UTR. Patients less likely to be responsive to treatment with a TS directed drug, e.g., 5-fluorouracil, were determined to be homozygous for this triple repeat of the tandemly repeated sequence. Patients exhibiting heterozygous genotype for a double repeat and a triple repeat of the tandemly repeated sequence. The patients most likely to respond to administration of a TS directed drug (e.g., 5-fluorouracil) are homozygous for a double repeat of the tandemly repeated sequence.

Even after successful treatment, local recurrence for patients with rectal cancer is a significant medical issue. Patients with localized rectal cancer are treated with radiation therapy to reduce the risk for local recurrence. The standard therapy for locally advanced rectal cancer either pre or post-operative is 5-FU chemotherapy and radiation therapy. Depending on the pathological staging the risk for tumor recurrence is between 10 and 60%. Identifying patients at high risk for tumor recurrence will allow the development of better treatment strategies for high risk patients. To this end, the 28 bp tandemly repeat polymorphism in the TS gene was found to be predictive of the risk of local recurrence in patients with rectal cancer treated either with pre or postoperative chemoradiation therapy is disclosed.

Methods: Forty-three (43) patients with locally advanced rectal cancer, who were treated with either pre-operative or post-operative 5-FU and pelvic radiation were analyzed. Genomic DNAs were extracted from paraffin-embedded tissue samples. Patients' genotype for the TS polymorphism was determined by polymerase chain reaction (PCR) amplification of TS promoter region. The PCR products were then electrophoresed, revealing bands of 220 bp (2/2), 248 bp (3/3) or both (2/3). The genotyping was repeated performed among 24 patients who developed local recurrence and 19 patients who did not.

Results: Pelvic recurrences were found in 87% patients homozygous for the triple tandemly repeated (3/3) genotype, compared to 37% patients heterozygous with (2/2) and (2/3), after either pre-operative or post-operative chemoradiation. P value is less than 0.01. However, the (3/3) genotype was not associated with advanced T or N stage, high grade histology, positive margin, or vascular space invasion, thus is an independent predictor for pelvic recurrence.

Thus, rectal cancer patients with 3/3 TS polymorphism are less likely to be controlled locally after combined 5-FU and pelvic radiation because of their resistance to both 5-FU and radiation. Other chemotherapeutic agents such as CPT-11 or oxaliplatin, in combination with radiation are alternatives therapies.

Example 3

TS 3' Polymorphism For Predicting Response And Survival To 5-FU And Oxaliplatin

This example shows that a polymorphism associated with the TS gene is associated with clinical response and survival to 5-FU/oxaliplatin chemotherapy in patients with cancer. Example 2, supra, reports that the polymorphism in the TS promoter is associated with TS gene expression in the normal tissue and the tumor tissue. The findings indicate that it is possible to predict TS gene expression in the tumor by measuring the TS polymorphism in peripheral blood cells. Recently a polymorphism has been described in the 3' end of the gene which have found to be associated with intratumoral gene expression. This TS polymorphism is associated with overall survival in patients treated with oxaliplatin and 5-FU and is an independent predictor of outcome.

Prediction of response to 5-FU based chemotherapy and prediction of optimal dose of 5-FU will maximize therapeutic benefits and minimize treatment risks. Polymorphisms of genes involved with the target of anticancer drugs and metabolism of anti-cancer drugs can be predictive of intratumoral gene expression levels. Polymorphism profiles can therefore influence the selection or dosing of chemotherapeutic drugs. While not wishing to be bound by any theory, the results reported herein also explain the differences in toxicities and efficacy of anticancer drugs in different ethnic groups since most of these polymorphisms have been shown to have ethnic group associated characteristic gene frequencies.

Methods: To investigate the functional relevance of this polymorphism, the relative TS mRNA level and the polymorphism in the 3'-untranslated region of the TS gene in 102 patients with advanced colorectal carcinoma treated with 5-FU and oxaliplatin in second or third line chemotherapy was evaluated. A polymerase chain reaction amplification/RFLP analysis was performed to identify the TS genotype using known methods known in the art. TS mRNA was quantitated using a quantitative RT-PCR method known in the art and described in Hankoshi T. et al. (1992) Cancer Res. 52:108-116.

The wildtype variant (+6 bp/+6 bp) was associated with highest TS mRNA expression in the tumor (11.35, 95% CI:6.43,20.03) when compared to the heterozygous variant (+6 bp/−6 bp) with a TS level of 5.42 (95% CI:3.57,8.24) and the homozygous mutant variant with TS 2.71 (95% CI: 1.18, 5.26) (p=0.017, F-Test, see Table 1).

TABLE 2

TS Genotype and TS mRNA Levels in Tumor Tissue

| Tissue | TS Genotype | N | % | TS Mean[1] | 95% CI[2] | Comparison of TS Means Genotype | p-value[3] |
|---|---|---|---|---|---|---|---|
| Metastatic tumor tissue (N = 43) | +6 bp/+6 bp | 13 | 30% | 11.35 | (6.43, 20.03) | +6 bp/+6 bp vs. −6 bp/−6 bp | 0.007 |
| | +6 bp/−6 bp | 24 | 56% | 5.42 | (3.57, 8.24) | +6 bp/+6 bp vs. +6 bp/−6 bp | 0.041 |
| | −6 bp/−6 bp | 6 | 14% | 2.71 | (1.18, 6.26) | +6 bp/−6 bp vs. −6 bp/−6 bp | 0.14 |
| | | | | | | Overall | 0.017 |

[1]TS mean = geometric mean of mRNA expression of TS relative to β actin mRNA
[2]95% confidence interval
[3]p-value for the overall comparison is based on the F-test, all other p-values are base on the LSD-Test (Least significant difference test).

The wildtype variant (+6 bp/+6 bp) was associated with a significant survival benefit when compared to the heterozygous variant (+6 bp/−6 bp) and the homozygous mutant variant (p=0.040 based on the cox proportional hazards model stratified by ECOG and multivariate analysis). Thus, this polymorphism in the 3' untranslated region is predictive of clinical response and outcome for some patients.

Example 4

ERCC1 Gene Polymorphism for Predicting Response and Survival to 5-FU/Oxaliplatin Chemotherapy The results shown below establish that polymorphism associated with the ERCC1 (excision repair cross complementation group 1) gene is associated with clinical response and survival to 5-FU/oxaliplatin chemotherapy in patients with cancer and with ERCC1 mRNA levels.

ERCC1 is a highly conserved enzyme, is specific to the nucleotide excision repair (NER)1 pathway and its absence is incompatible with life. Among the proteins involved in the NER, a defect in the ERCC1 seems to be associated with the most severe DNA repair deficiency.

Platinum compounds are becoming mainstay chemotherapy treatment for gastric, ovarian, and colorectal cancer, among others. Among its mechanisms of resistance, increased DNA repair seems to be the most important mechanism.

Studies have shown that increased ERCC1 mRNA levels are directly related to clinical resistance to cisplatin in human ovarian cancer as well as cervical cancer. It has previously been shown that ERCC1 mRNA levels are also directly correlated to clinical resistance to 5-FU and cisplatin in gastric cancer patients. It has also recently been shown that intra-tumoral ERCC1 mRNA levels are able to predict clinical response and overall survival in patients with metastastatic colorectal cancer treated with 5-FU/oxaliplatin.

The ERCC1 gene contains a very common polymorphism at codon 118 (exon 4). This polymorphism is a single nucleotide change C→T which results in the same amino acid, asparagines. This change converts a codon of common usage (AAC) to a less used codon (AAT). The reported usage frequency of the latter is two-fold less than the former. A study using ovarian cancer cell lines showed a 50% reduction in DNA adduct repair in a cell line containing the polymorphism compared to the "wild-type." However, they were found to be equally resistant to platinum.

In this study the ERCC1 polymorphism at codon 118 and intra-tumoral ERCC1 mRNA levels of 32 patients with metastatic colorectal cancer treated with 5-FU/oxaliplatin was assessed. The median mRNA level was 2.95. Three of eleven (27.3%) patients with the C/C genotype had ERCC1 mRNA levels greater than 2.95, whereas 5 out of 12 (41.7%) and 7 out of 9 (77.8%) of patients with the C/T and T/T genotype respectively. When the mRNA levels of patients containing the C allele was compared to those without the C allele, the difference was statistically significant (p=0.049).

In a related study, the ERCC 1 polymorphism at codon 118 and the overall survival of 60 patients with metastatic colorectal cancer treated with 5-Fu/oxaliplatin was also assessed. The median survival of patients was 531 days for those with the C/C genotype, 254 days for the C/T genotype, and 256 days for the T/T genotype (trend p=0.089). The relative risk ratio for death was 2.12 for the C/T and 2.36 for the T/T genotype. The median survival of patients containing the T allele was 256 days and those without was 531 days (p=0.056).

A search of the literature failed to provide an explanation of how a "silent" polymorphism that results in a codon of lesser usage can be associated with higher levels of mRNA. Without being bound by any theory, Applicants note that this polymorphism is associated with ERCC 1 mRNA levels and therefore can predict survival in patients with metastatic colorectal cancer treated with 5-FU/oxaliplatin.

Example 5

XPD (ERC2) Gene—Polymorphism for Predicting Response and Survival to Platinum Based Chemotherapy The results shown below establish that polymorphism associated with the XPD gene is associated with clinical response and survival to platinum based chemotherapy in patients with cancer.

The XPD protein is essential in transcription and a major participant in the nucleotide excision repair (NER) pathway. Several polymorphisms in the XPD gene have been identified. However, their functional sionilicance has not been elucidated. A single nucleotide polymorphism in codon 751 (A→C) causes an amino acid change Lys→Gln There is evidence that the polymorphism at codon 751 may affect DNA repair capability, although previous studies regarding this issue have shown conflicting results. (See Heidelberger, C. et al. (1957) Nature 179:663-666 and Horie, N. et al. (1995) Cell Struct. Funct. 20:191-197).

Increased DNA repair is a well-established mechanism for chemo-resistance to platinum based compounds such as oxaliplatin. The results reported herein show that increased gene expression of ERCC1 (a member of the NER enzyme family) is associated with resistance to 5-FU and cisplatin chemotherapy in gastric cancer patients.

Methods: The XPD codon 751 polymorphic status of 69 patients with metastatic colorectal cancer who previously had failed 5-FU based chemotherapy and determined their response and overall survival to 5-FU/oxaliplatin combination treatment. Genotyping was done on white blood cells using the RFLP-PCR method.

Sixty seven patients were evaluated for response. The overall response rate was 15% (10/67). 25% (5/20) patients with the Lys/Lys genotype responded, compared to 11% (4/37) and 10% (1/10) of those with the Lys/Gln and Gln/Gln genotypes respectively (p=0.007 Fisher's exact test, two-tailed). More significantly, among those with the Gln/Gln genotype, 50% (5/10) had progressive disease compared to 10% (2/20) and 5% (2/37) of patients with the Lys/Lys and Lys/Gln genotypes respectively.

The overall survival and its relation to the polymorphism was also evaluated. For patients with the Lys/Lys genotype the median survival was 530 days. Those with the Lys/Gln genotype had a median survival of 356 days. Finally, those with the Gln/Gln genotype had a median survival of 186 days (p=0.06 for trend). Thus, the R.R. of death was 1.00 of the Lys/Lys group, 1.49 for those with Lys/Gln, and 3.01 for the with Gln/Gln.

Results: The mechanism through which the Lys751Gln polymorphism of the XPD gene affects DNA repair capacity and resistance to chemotherapy is unknown. In fact, its very role in DNA repair capacity is still being debated. Studies have shown conflicting results on whether the polymorphism is associated with increased or decreased DNA repair capacity. (See Heidelberger, C. et al. (1957) Nature 179:663-666 and Horie, N. et al. (1995) Cell Struct. Funct. 20:191-197).

These results show the XPD gene plays an important role in chemo-resistance and genotyping. The 751 polymorphism is useful in the prediction of clinical response, survival and clinical toxicity to platinum based chemotherapy, as well as the design of novel agents that modulate XPD function. XPD is also an important target for drug development.

Example 6

XRCC1 Polymorphism is Predictive of Response in Patients Treated with Platinum-Based Chemotherapy Recently, Divine et al. (Proceedings AACR Annual meeting March 2000, page 591) demonstrated that XRCC-1 polymorphism are associated with higher AFB1-adducts and GPA somatic mutations but also associated with lung cancer risk, colon cancer risk in Egyptian (Abdel-Rahman et al. Proceedings AACR, Annual Meeting, March 2000, page 595) and prostate cancer risk (Hu et al. Proceedings AACR Annual Meeting, March 2000, page 596). A polymorphism in exon 6 has been shown to have a protective effect against bladder cancer development (Stem et al., Proceedings, AACR Annual meeting March 2000, page 592).

XRCC-1 plays a central role in single strand break repair and base excision repair. In addition, at least one of the gene products required for single strand break repair in mammals, the XRCC1 polypeptide is required for viability in mice, mutant cells lacking XRCC-1 display cellular sensitivity to ionizing radiation and alkylating agents and exhibit elevated spontaneous frequencies of chromosome aberration. (Caldecott et al., Proceedings AACR Annual Meeting, March 2000, page 891).

Methods: Forty-five (45) patients with advanced colorectal cancer patients with 5-FU and oxaliplatin who failed at least one prior chemotherapy regimen were selected. XRCC-1 polymorphisms and their association with clinical outcome in patients with metastatic colorectal cancer treated with 5-FU and oxaliplatin were studied. These patients were heavily pretreated but received a platinum compound for the first time. To determine whether variation in the XRCC-1 DNA repair genes is related to host DNA damage, the association between polymorphisms in XRCC1 (codon 399) and sister chromatid exchange (SCE) frequencies (n=76) and polyphenol DNA adducts (n=61) was studied. XRCC1 genotype was identified using PCR-RFLP.

Results: From 45 patients, 6 patients (13%) underwent a partial response, 30 patients (67%) had stable disease and 9 (20%) had progressive disease. 18 patients had an A/A polymorphism, 22 an A/G and 5 a G/G polymorphism. From the 6 responders, 5 have had an A/A polymorphism and one an A/G polymorphism. 3 from 9 patients with progressive disease had a G/G polymorphism and 4 from these 9 had an A/G polymorphism. Using the Jonckheere-Terpstra Test (monte carlo two sided test) the p value was statistically significant with 0.0063 with the 99% confidence interval of 0.0043 and 0.0083. These data demonstrate that the A/A polymorphism is associated with response to chemotherapy and patients with a G/G polymorphism are associated with resistance to platinum compounds.

Mean SCE frequencies among current smokers who were homozygous carriers of the 399Gln allele in XRCC1 were greater than those in 399Arg/Arg current smokers. A possible gene-dosage effect for XRCC1 399Gln and detectable DNA adducts was described, and significantly more adducts among older subjects who were carriers of the 399Gln allele than in younger subjects with the 399Arg/Arg genotype suggesting that carriers of the polymorphic XRCC1 399Gln allele maybe at greater risk for DNA damage. (Carcinogenesis (Oxford) 21(5)(2000):965-971).

Applicants have discovered that the XRCC-1 gene predicts response in patients treated with platinum-based chemotherapy. Identification of XRCC-1 polymorphism allowed not only to decide whether platinum will have benefit but also may determine the risk of side effects with platinum. XRCC-1 polymorphism could allow a personalized approach to therapy—individualization of the dose and choice of the anticancer drug based on use of this pre-screen. The studies reported herein also identify individuals likely who have benefit from platinum based chemotherapy and likely to experience side effects of platinum agents.

Example 7

Human Glutathione S-Transferase P1 Polymorphism is Predictive of Survival of Patients with Advanced Colorecal Cancer Treated with 5-FU/Oxaliplatin Chemotherapy Glutathione transferases consist of a super-family of phase II metabolic enzymes that catalyze the conjugation of reduced glutathione. The detoxifying character of these reactions is responsible for the protection of cellular macromolecules from damage caused by carcinogenic and cytotoxic agents. (See Mannervik, B. (1985) Adv. Enzymol. 57:357-417). GSTP1-1 has been shown to be widely expressed in human epithelial tissues and to be over-expressed in several tumors including colon tumors. (Terrier P. et al. (1990) Am. J. Pathol. 137:845-853; Moscow J. A. et al. (1989) Cancer Res. 49:1422-1428; Howie A. F. et al. (1990) Carcinogenesis 11:451-458; Peters W. M. et al. (1992) Gastroenterology 103: 448-455; and Singh S. V. et al. (1990) Cancer Lett. 51:43-48). Increased levels in tumors may be in part responsible for the observed resistance to chemotherapy as it has been found in several tumors, but the mechanism still remains unknown. (Tsuchida S. et al. (1992) Rev. Biochem. Mol. Biol. 27:337-384). Factors that influence the expression level of GSTP 1 may become important tools to predict therapy response and survival of patients treated with certain drugs or drug combinations. A G→A transition in exon 5 at nucleotide 313 leads to an amino acid exchange in the protein from isoleucin to valine; as previously reported by Board et al. (1989) Ann. Hum. Genet. 53:205-213. In-vitro cDNA expression studies revealed an association between this amino acid change and a reduced activity level of the GSTP1 enzyme. (Zimniak P. et al. (1994) Eur. J. Biochem. 224:893-899). Recently it has been found that the 105Val allele variant of the GSTP1 gene at exon 5 is associated with a low GST enzyme activity in normal lung tissue and esophageal Barrett's epithelium. (Watson M. A. et al. (1998) Carcinogenesis 19:275-280 and Van Leishout, E. M. M. (1999) Cancer Res. 59:588-589). Additionally, it has been shown that the 105Val allele is associated with increased risk for testicular, bladder cancer and esophageal carcinoma, but not for colon or breast cancer. (Harries L. W. (1997) Carcinogenesis 18:641-644).

Furthermore, this Ile105Val substitution has been shown to be associated with better survival in women with breast cancer who received chemotherapy (cyclophosphamide, 5-FU, adriamycin) (Sweeney C. (2000) Cancer Res. 60:5621-5624). Nishimura et al. (Nishimura T. et al. (1998) Chem. Biol. Interact. 111:187-198) showed that the response rate of patients with head and neck cancer receiving platinum-based chemotherapy was significantly higher for patients with low GST protein expression. Based on these encouraging data 81 patients with advanced colorectal tumors that received combination chemotherapy of 5-FU/oxaliplatin were genotyped.

Methods and Results: In this study, 81 patients with advanced colorectal cancer, who received 5-FU/oxaliplatin chemotherapy as a third line treatment, after failing 5-FU and CPT-11 were screened for the polymorphism at exon 5 of the GSTP1 gene. The median overall survival time was 10.2 months (95% Cl:7.9,13.3) with a median follow up time of 11 months (95% CI: 1.1,15.3). Patients with a VALVAL genotype had a significant survival benefit compared to patients heterozygous or homozygous for the ILE allele (p=0.028, Logrank Test). Patients that are homozygous for the VAL allele had a probability of survival at 18 months of 0.89, compared to 0.40 for patients heterozygous and only 0.06 for patients homozygous for the ILE allele. Patients homozygous for the ILE allele showed a 5.4 fold increased relative risk of dying when compared to the VALVAL group (Table 3). Patients homozygous for the ILE allele had a median survival of 7.9 months (95% CI: 5.9,12.8) compared to 13.3 months (95% CI: 8.4,23.7) for heterozygous. Patients homozygous far the VAL allele survived 24+ months (95% CI: NA) (p=0.028, Logrank Test, Table 4).

TABLE 3

Univariate Analysis of Survival of Patients with Colon Cancer

| Factors | No. Patients | Relative Risk[1] | 95% CI[2] | Probability of Survival at 18 months | p-Value[3] |
|---|---|---|---|---|---|
| GST-P1 | | | | | 0.028 |
| VAL/VAL | 9 | 1.00 | | 0.89 ± 0.10 | |
| ILE/VAL | 37 | 2.73 | (1.43, 5.23) | 0.40 ± 0.11 | |
| ILE/ILE | 35 | 5.40 | (2.83, 10.30) | 0.06 ± 0.06 | |
| GST-P1 | | | | | 0.011 |
| Any VAL | 46 | 1.00 | | 0.44 ± 0.11 | |
| ILE/ILE | 35 | 2.12 | (1.15, 4.18) | 0.06 ± 0.06 | |
| GST-P1 | | | | | 0.14 |
| VAL/VAL | 9 | 1.00 | | 0.89 ± 0.10 | |
| Any ILE | 72 | 3.93 | (0.55, 28.23) | 0.21 ± 0.07 | |

[1]Relative risk can be thought as the average increased chance of dying at any point in time for patients in the second group compared to those In the first group. The group with better prognosis is listed first.
[2]95% confidence interval
[3]Based on logrank test.

TABLE 4

Association between genotype of the GSTPI gene and survival of patients with advanced colorectal cancer

| Genotype | No. of Patients | Median Survival | 95% CI[1] | p-value[2] |
|---|---|---|---|---|
| ILE/ILE | 35 | 7.9 months | (5.9, 12.8) | 0.028 |
| ILE/VAL | 37 | 13.3 months | (8.4, 23.7) | |
| VAL/VAL | 9 | 24+ months | (NA) | |

[1]95% confidence interval
[2]Based on logrank test.
Overall median time survival and its 95% CI: 10.2 (7.9, 13.3) months
Overall median time follow up and range: 11.0 (1.1, 25.3) months
The survival far this study is not related to GENDER and ETHNICITY.

Applicants show a significant association between survival and the Ile105Val polymorphism at exon 5 of the GSTP1 gene. Patients homozygous for the amino acid substitution had a significant survival benefit. According to previous in-vitro reports and studies in different human tissues the Val/Val genotype is associated with a lower GST enzyme activity compared to the heterozygous and the ILE/ILE genotype (Zimniak P. et al. (1994) supra; Watson M. A. et al., (1998) supra; and Van Lieshout (1999), supra). Considering these results, patients with the VAL/VAL genotype and respectively a lower GST enzyme activity benefit from treatment with 5-FU/oxaliplatin compared to heterozygotes and the ILE/ILE genotype group. A lower GST enzyme activity is thought to be less efficient in glutathione conjugation of drug intermediates, which leads to a longer and most likely more efficient exposure of the active drug to the tumor cell. This might explain the survival benefit for patients with two or at least one VAL allele compared to the ILE/ILE genotype.

To Applicants' knowledge, this is the first report of the role of the ILE105VAL polymorphism of the GSTP1 gene and patients with metastatic colorectal cancer, which received 5-FU/oxaliplatin chemotherapy. This GSTP1 polymorphism can be become a useful marker to identify patients with an increased risk to fail this third-line chemotherapy, thus sparing those heavily pretreated patients the side effects of a 5-Fu/oxaliplatin therapy and refer them to other therapy alternatives. The procedure of a simple blood test may be enable the clinician to design more individualized chemotherapy.

Example 8

A Polymorphic Dinucleotide Repeat in Intron 1 of EGFR Gene is Associated with Clinical Response to Platinum Based Chemotherapy in Patients with Advanced Colorectal Disease EGFR is a 170-kD transmembrane glycoprotein whose gene is located on the short arm of human chromosome 7p12. It is a member of the receptor protein tyrosine kinase family with several extracellular growth factor ligands, including epidermal growth factor (EGF), and TGF-$\alpha$. EGFR are frequently over expressed in many types of human cancers, including CRC (colon and rectal cancers) and their over expression typically confers a more aggressive clinical behavior. (Salomon, D. et al. (1995) Critical Reviews in Oncology-Hematology 19:183-232).

The level of EGFR expression is primarily regulated by the abundance of its mRNA and the nature of the EGFR over expression is believed to be due to an increase in the rate of EGFR transcription. (Grandis, J. R. and Tweardy, D. J. (1993) Cancer Res. 53:3579-3584). Recently, study shows that EGFR gene transcription activity declines with increasing numbers of a highly polymorphic dinucleotide repeat (CA repeat) in Intron 1(Gebhardt F. et al. (1999) J. Bio. Chem. 274:13176-13180).

The EGFR polymorphic dinucleotide repeat (CA repeat) of 78 patients to with metastatic colorectal cancer who previously had failed 5-FU based chemotherapy was assessed to determine their response and overall survival to 5-FU/oxaliplatin combination treatment. The number of CA repeats was determinated by 5'-end labeled polymerase chain reaction using forward primer 5'-GTTTGAAGAATTTGAGC-CAAAC-C 3' (SEQ ID NO. 1) and reverse primer: 5'-TTCT-TCTGCACACTTGGCAC 3' (SEQ ID NO. 2). The reaction was incubated for 28 cycles with denaturation at 94° C. for 1 minute, annealing at 55° C. for 1 minute, and extension at 72° C. for 2 minutes. The reaction products were separated on 6% denaturing polyacrylamide DNA sequencing gels, vacuum blotted and exposed to Kodak XAR film ovenight using well known procedures as described in Chi, D. D. et al. (1992) Human Molecular Genetics 1:135.

Thirty-eight patients were evaluated for response. The overall response rate was 18% (7/38). 56% (4/9) patients were found with the 16/16 repeats progressed, compared to 6%

(1/17) and 8% (1/12) of those with 16/18 repeats and 16/20 repeats respectively (p=0.008 Fisher's exact test, two-tailed). The overall survival and its relation to the polymorphism were also evaluated. For patients with the 16/16 repeats the median survival was 66 days. Those with the 16/18 repeats had a median survival of 179 days. Finally, those with the 16/20 repeats had a median survival of 805 days (p=0.1 for trend).

This report shows that short CA repeats (16/16) increase the EGFR gene transcription and overexpressed the gene. Thus short CA repeats (16/16) have a poor prognosis compare with long CA repeats (16/20).

Example 9

Epidermal Growth Factor Receptor (EGFR) Gene Expression and Polymorphism Predict Pelvic Recurrence in Patients with Rectal Cancer Treated with Chemoradiation EGFR is frequently overexpressed or mutated in many types of cancer including colorectal cancer. EGFR overexpression is associated with more aggressive tumor behavior and poor tumor response to cytotoxic agents and radiation. In vitro and clinical studies have associated EGFR overexpression with radioresistance. Example 8, above, shows that a dinucletide repeat length polymorphism in intron 1 of the EGFR gene was associated with response to 5-FU/oxaliplatin in patients with metastatic colorectal cancer. In vitro data also suggest that this genomic polymorphism is associated with expression levels of EGFR.

Methods: Seventy-three patients with locally advanced rectal cancer (UICC stage II and III) were treated with adjuvant radio-chemotherapy. There were 25 (34.2%) women and 48 (65.8%) men with a median age of 52 years (range 25, 79 years). Thirty-one patients (42.5%) developed local tumor recurrence during the follow up time. The tumors were graded histopathologically as highly differentiated (G1; 1 patient) moderately differentiated (G2; 56 patients), and poorly differentiated (G3; 16 patients). Histological staging revealed 22 patients stage T2, 51 patients stage T3. Thirty-five (35) patients were lymph node negative, 38 had lymph node metastases. No patient had systemic metastases at the time of first diagnosis. Ethnic background: 50 patients Caucasian, 13 Hispanic, 8 Asian, 2 African-American. Patient data were collected retrospectively. Informed consent was signed by all patients involved in the study. Patients underwent lower anteriorer resectomy (LAR; n-44), abdominal perineal resectomy (APR; n=20), or transanal resectomy (TR; n=9), followed by 5-FU infusion plus pelvic radiation. Pelvic irradiation was given as a dose of 45 Gy to the whole pelvis and an additional boost up to 54 Gy.

Samples for gene expression analysis were obtained during the surgical procedure. All samples were formalin-fixed and paraffin-embedded. All paraffin embedded specimens underwent laser-capture-microdissection in order to isolate RNA from tumor tissue and adjacent normal tissue. RNA isolation after dissection was done according to U.S. Pat. No. 6,248, 535. Following RNA isolation, cDNA was prepared from each sample. Quatification of cDNA and an internal reference gene (beta [β]-actin) was conducted using a fluorescence-based real-time detection method (ABI PRISM 7900 Sequence Detection System [TaqMan®]; Perkin-Elmer Applied Biosystems, Foster City, Calif.). The PCR mixture consisted of 600 nmol/L of each primer, 200 nmol/L probe (sequences used are given below), 5 units of AmpliTaq® Gold polymerase, 200 μmol/L each of dATP, dCTP, and dGTP, 400 μmol/L dTTP, 3.5 mmol/L MgC12, and 1× TaqMan® buffer A containing a reference dye, to a final volume of 20 μL (all reagents were supplied by Perkin-Elmer Applied Biosystems). Cycling conditions were 50° C. for 10 seconds and 95° C. for 10 minutes, followed by 46 cycles at 95° C. for 15 seconds and 60° C. for 1 minute. Colon, liver, and lung RNAs (all Stratagene, La Jolla, Calif.) were used as control calibrators on each plate. Blood sample was collected from each individual and genomic DNA was extracted from peripheral blood lymphocytes using the QiaAmp kit (Qiagen, Valencia, Calif.). EGFR microsatellite analysis was done according to well known procedures. Briefly, standard PCR reactions were performed with 5'-$^{33}$P-γATP end-labeled forward primer according to well known methods and the reaction products were separated on 6% denaturing polyacrylamide DNA sequencing gel, vacuum blotted and exposed to XAR film (Eastman-Kodak Co., Rochester N.Y.) for overnight. Exact number of EGFR CA repeat was confirmed by direct sequence the PCR product.

Conclusion: A significant association between pelvic recurrence and EGFR gene expression levels was found in rectal normal tissues. Patients with high EGFR gene expression levels had a higher(3.8 fold) relative risk for pelvic recurrence compared with those have low EGFR gene expression levels (p=0.022 logrank test) treated with chemoradiation. A trend of possible relationship (P=0. 17 logrank test) exists between dinucleotide repeat length polymorphism in intron 1 of the EGFR gene and time to local recurrence in rectal cancer patients. Patients with shorter (CA)n repeat (both CA repeat<20) have a shorter time to local recurrence compared with those with longer (CA)n repeat (both CA repeat>20). EGFR gene expression levels in tumor tissue do not have statistical significance to predict time to local recurrence in rectal patients treated with chemoradiation.

This is the first study that shows EGFR gene expression levels in normal rectal tissue and the dinucleotide repeat length polymorphism in intron 1 of the EGFR gene may be associated with time to local recurrence in rectal cancer patients treated with chemoradiation. These data suggest that EGFR gene expression levels in normal rectal tissues and EGFR gene polymorphism can identify patients at high risk for pelvic recurrence.

Example 10

COX-2 Prevents Clinical Toxicity Associated with Chemotherapy

Prostaglandines (PG) are formed by the action cyclooxygenase (COX). Two related isoforms, COX-1 and COX-2 transform arachidonic acid to prostaglandins, but they differ in their physiological roles and distribution (Smith W. L. et al. (1996) J Biol Chem. 271:33157-33160). COX-1, a constitutive isoform is present in many cell types throughout the human body and is specifically responsible for the maintaining of gastric mucosa by production of cytoprotective prostanoids, appropriate platelet function, and renal blood flow.

The inducible isoform COX-2, has been shown to be absent under normal conditions, but to be induced by cytokines, growth factor, mitogenes and tumor promotors and to be responsible for mediation of inflammation, fever, tumor growth and pain. (Hla T. and Neilson K. (1992) Proc Natl Acad Sci USA 89:7384-7388 and Jones D. A. et al. (1993) J. Biol. Chem. 268:9049-9054).

Classic NSAIDs inhibit both isoforms at standard anti-inflammatory doses. The inhibition of COX-2 explains the therapeutic effects since it is involved in the formation of PG that mediates pain and inflammation. But unwanted side effects such as gastric toxicity, mild bleeding diathesis, and renal dysfunction also occur, because of the concurrent inhibition of COX-1. (Dannhardt G. and Kiefer W (2001) Eur. J. Med. Chem. 36:109-126). Recently, selective inhibitors of cyclooxygenase-2, have been proven to exert therapeutic efficacy without these unwanted side effects (Reddy B. S. et al. (1996) Cancer Res. 56:4566-4569).

Since cancer patients, especially in advanced stages of the disease, often experience tremendous pain, drugs are needed that provide effective relief. But it has to be considered that side effects from these painkillers may interfere with the toxicity that is caused by the necessary chemotherapy. Since the prostaglandin pathway plays a significant role in secretory diarrhea, inhibition of COX-2 may in fact decrease diarrhea caused by chemotherapy. (Beubler E. and Schuligoi R. (2000) Annals of the New York Academy of Sciences. 915:339-46). Animal data suggest that COX-2 inhibition in fact can inhibit or prevent chemically induced neurotoxicity in brain of rats suggesting a potential role of COX-2 in neurotoxicity. (Kunz T. and Oliw E. H. (2001) Eur. J. of Neuroscience 13(3):569-75 and Hewett S. J. et al. (2000) J. Pharmacology & Experimental Therapeutics 293(2):41 7-25).

Selective COX-2 inhibitors will be most beneficial symptomatic treatment for the patient, who receives chemotherapy for two reasons. First, the patient's pain will be reduced since COX-2 inhibitors block the formation of pain and inflammation mediating prostaglandins. Second, the formation of cytoprotective prostaglandins in the gastrointestinal tract will not be altered. The physiological protection against aggressive compounds such as acid and agents from chemotherapy regimens will be kept. This may result in less side effects from chemotherapy. Additionally, it has been suggested that the rate-limiting enzyme in the PG pathway, COX-2, which is highly expressed in many tumors (Bae S. H. et al. (2001) Clin. Cancer Res. 7:1410-1418) is associated with the carcinogenesis process in colorectal cancer (Sano H. et al., Cancer Res. 55: 3785-3789 and Hao X. (1999) et al. (1999) J. Pathol. 187:295-301). The induction of colorectal tumors by azzoxymethane has been shown to be nearly complete suppressed by selective COX-2 inhibition (Kawamori T. et al. (1998) Cancer Res. 58:409-412) and colon polyps showed regression after treatment with non-selective NSAIDs (Giardiello F. M. et al. (1993) N. Engl. J. Med. 328:1313-1316).

In a retrospective analysis, Applicants have identified that celebrex at doses between 200-400 mg day is protecting against neurotoxicity in patients treated with oxaliplatin. In the analysis of 156 patients, 90 of which had no celebrex treatment in combination with oxaliplatin and 5-FU, 26 of these patients developed grade II or III neurotoxicity, from the 56 patients who had celebrex therapy in combination with oxaliplating/5-FU chemotherapy, only 3 developed grade II or lit neurotoxicity. This is highly statistically significant ($p<0.01$).

Example 11

Functional Polymorphisms of Matrix Metalloproteinases Can Predict Distant Metastases in Patients with Advanced Colorectal Cancer Matrix metalloproteinases (MMPs) are members of a family of zinc-dependent enzymes involved in the degradation of extracellular matrix (ECM). In vitro studies have shown that the MMPs are able to degrade an array of connective tissue proteins, suggesting that these enzymes may play a role in connective tissue destruction and formation associated with various pathological processes including cancer invasion and metastasis, cartilage destruction in arthritis, atherosclerotic plaque rupture, and the onset of aneurysms.

Naturally occurring sequence variation has been discovered in the promoter regions of a number of MMP genes, including MMP-1 (-1607 1 G/2G), MMP-3 (-1612 5A/6A), and MMP-9 (-1562 C/T). These germline polymorphisms have been shown to have allele-specific effects on the transcriptional activities of these MMP gene promoters.

In fact, ovarian tumor tissues from patients possessing the 2G allele within the promoter of the MMP-1 (collagenase-1) gene have been shown to express more MMP-1 compared to those from patients not carrying the 2G allele. (Kanamori Y. et al. (1999) Cancer Research 59:4225-4227). Insufficient MMP-3 (stromelysin-1) expression has been attributed to the presence of 6A allele within the gene promoter leading to vascular matrix, and a study has demonstrated that the 6A/6A genotype is associated with increased carotid artery wall thickness measured using non-invasive ultrasonography. (Gnasso A. et al. (2000) Arterioscler. Thromb. Vasc. Biology 20:1600-1605). In a cohort study of Caucasian patients with coronary atherosclerosis, a correlation of the C-1562T polymorphism of MMP-9 (gelatinase B) gene with severity of the disease has been identified, and this association may be due to enhanced ability of vascular smooth muscle cells to migrate and proliferate during atherogenesis in individuals possessing the T allele. (Zhang B et al. (1999) Circulation 99:1788-1794).

Methods: From 1998 through 2000,472 patients with advanced colorectal cancer who were treated at University of Southern California/Norris Comprehensive Cancer Center were identified. Of these 472 patients, the association between the polymorphisms of MMP-1, MMP-3, and MMP-9 and site of metastases in 60 participants who were eligible for the analysis of present study were examined. This study was investigated at the Norris comprehensive Cancer Center and approved by the Institutional Review Board (IRB) of the University of Southern California for Medical Sciences. The age, ethnicity, and follow-up information for each subject were obtained from the retrospective chart reviews.

A blood sample was collected from each patient and the corresponding genomic DNA was extracted from the peripheral blood lymphocytes using the QiaAmp kit (Qiagen, Valencia, Calif., USA). All samples were evaluated using a PCR-RFLP technique. After restriction enzyme digestion, PCR products were visualized on a 4% agarose gel and analyzed.

Results For the study participants, 10 patients only had peritoneal carcinomatosis with a median follow-up of 17 months (95% CI, 10.6-25.3 months) before tumor progression; and 50 patients who presented liver and/or lung metastases had a median follow-up of 34.3 months (95% CI, 11.6-61.3 months) before tumor progression. Of these patients, the median age was 55.3 years (36.2-91.1 years) and the median follow-up was 30.1 months (95% CI, 10.6-61.3 months).

The analyses of MMP-3 and MMP-9 polymorphisms failed to show statistical significance ($p=0.18$ and $p=0.69$, respectively). However, the presence of 2G allele, which has been implicated in higher transcription rate of MMP-1 gene, was associated with site of metastases when patients with peritoneal disease were compared to those with distant metastases ($p=0.08$).

Fourteen patients (23%) possessed the MMP-1 1G/1G genotype, 15 patients (25%) had 2G/2G genotype, and 30 patients (50%) were heterozygous for this variant. Of the study participants with only peritoneal carcinomatosis, 40% (4/10) had the 1G/1G genotype, while 0% (0/10) of those with 2G/2G genotype and 60% (6/10) of those heterozygous showed evidence of local disease. Of the patients who had distant metastases, 20% (10/49) carried the homozygous 1G allele compared to 31% (15/49) with homozygous 2G allele and 49% (24/49) with heterozygous genotype.

The 2G allele has been associated with deep invasive primary tumors, and therefore, poorer prognosis in patients with cutaneous malignant melanoma (CMM), suggesting that the aggressiveness of CMM is influenced by variation in the MMP-1 gene promoter. (Ye S. et al. (2001) Cancer Research 61:1296-1298). MMP-1 expression has been implicated as a novel marker for hematogenous metastasis of colorectal cancer, implying that its inhibition may be a strategy for prevention of metastasis. (Sunami E. et al. (2000) The Oncologist 5:108-114). MMP-1 immunoreactivity has also been significantly correlated with lymph node and hepatic metastases, tumor growth pattern, and additionally with the presence of lymphatic, venous, and neural invasions. (Shiozawa J. et al. The U.S. and Canadian Academy of Pathology 13(9):925-933).

Thus, the inheritance of the 2G allele is shown to be associated with invasiveness of colorectal cancer and distant metastases. Particularly, patients carrying homozygous 2G allele can be more genetically susceptible to developing distant metastases due to increased degradation of ECM, facilitating angiogenesis.

Example 12

Association Between Genetic Polymorphisms of Interleukin-8(IL-8) and Its Receptor CXCR1 and Survival of Patients with Metastatic Colorectal Cancer Treated with 5FU/Oxaliplatin Interleukin 8(IL-8) a member of the CXC chemokine family is known to be involved in tumor cell growth and metastasis in colorectal cancer. (Xie K. (2001) Cytokine Growth Factor Rev 12(4):375-91.) Its receptors CXCR1 and CXCR2 have vital roles in tumor progression and angiogenesis. (Miller L. J. et al. (1998) Anticancer Res. 18(1A):77-81). Studies show that expression of IL-8, CXCR1, and CXCR2 contribute to tumor progression and metastases in vitro and in vivo. (Brew R. et al. (2000) Cytokine 12(1):78-85) and Li A. et al. (2001) Clin. Cancer Res. 7(10):3298-304). Polymorphisms in the promoter region of IL-8 gene (T-251A) and a novel polymorphism in exon 2 of CXCR1 gene (Ser+ 2607Thr) may influence the expression of IL-8 and its receptor and therefore influence clinical outcome of patients with metastatic colorectal cancer. (Hull J. A. et al. (2000) Thorax 55(12):1023-7 and Renzoni E. et al. (2000) Arthritis Rheum 43(7):1633-40) The hypothesis that patients with genomic polymorphisms associated with higher expression or activity of Interleukin would have poorer prognosis was tested.

Patients were enrolled in the compassionate oxaliplatin protocol 3C-98-3 at the University of Southern California/Norris Comprehensive Cancer Center from 1998-2000. The chemotherapeutic regimen was as follows: 130 mg/m$^2$ oxaliplatin every three weeks and continuous infusion 5-Fu (200 mg/m$^2$/d). All patients had failed a prior treatment with 5-FU and 79% failed an additional second line treatment with irinotecan (CPT-11). Survival was determined from the start day of the 5-FU/oxaliplatin chemotherapy to death. Time to progression was determined from the start day of chemotherapy to the day the patient was taken off study due to disease progression. Patients who were alive at the last follow-up evaluation were censored at that time. Responders to therapy were classified as those patients whose tumor burden decreased by 50% or more for at least six weeks. Progressive disease was defined as 25% or more increase in tumor burden or the appearance of new lesions. Patients who did not experience a response and did not progress within the first 12 weeks following start of 5-FU/oxaliplatin, were classified as having stable disease. Four patients dropped out of the study too early for evaluation of response but they were included for the determination of survival.

A blood sample was collected from each individual and genomic DNA was extracted from peripheral blood lymphocytes using the QiaAmp kit (Qiagen, Valencia, Calif.). IL-8 and CXCR1 polymorphisms were done using PCR-RFLP.

Results: The overall response rate in patient groups was 9%. Only 16 patients remain alive and the follow-up from 6 to 18 months. Median survival was 9.4 months (95% C.I.7.6-12.8) and median time to progression was 5.0 months (95% C.I.4.4-6.5).

A significant relationship (P<0.05) was found between CXCR1 exon 2 Ser +2607 Thr polymorphism and the overall survival of patients with colorectal cancer treated with 5-FU/oxaliplatin after stratified by ECOG, histology or prior CPT-11 treatment.

Patients with the CXCR1 GC genotype had the 2.35 fold of relative risk of dying compared to patients with GG genotype after stratified by ECOG, histology or prior CPT-11 treatment. There is no significant relationship between IL-8 promoter polymorphism and overall survival. Also, there is no significant relationship between clinical response and both polymorphisms.

This is the first time study shows the IL-8 receptor CXCR1 Ser +2607 Thr polymorphism can be associated with overall survival in colorectal cancer patients treated with platinum-based chemotherapy.

The preceding examples are intended to illustrate, but not limit, the inventions as described herein.

We claim:

1. A method for selecting a therapy comprising administration of 5-Fluorouracil and oxaliplatin to treat a human metastatic colorectal cancer patient, the method comprising screening a nucleic acid sequence at codon 118 of the ERCC1 gene isolated from a cell or tissue sample isolated from said patient for the genotype at codon 118 of the ERCC1 gene, wherein the therapy is selected for the patient based on the presence of the genotype (C/C) or the therapy is not selected for the patient based on the presence of the genotype (C/T) or (T/T) at codon 118.

2. The method of claim 1, wherein the therapy further comprises radiation therapy.

3. A method for determining whether a human metastatic colorectal cancer is likely to experience longer survival following treatment with a therapy comprising the administration of 5-Fluorouracil and oxaliplatin, comprising screening a nucleic acid sequence at codon 118 of the ERCC1 gene in a cell or tissue sample isolated from said patient, and wherein the presence of the genotype (C/C) at codon 118 of the ERCC1 gene determines that said patient is likely to experience longer survival following treatment with said therapy as compared to patients receiving the therapy not having the genotype (C/C) of the ERCC1 gene.

4. The method of claim 3, wherein the therapy further comprises radiation therapy.

5. A method for determining whether a human metastatic colorectal cancer patient is likely to experience shorter survival following treatment with a therapy comprising the administration of 5-Fluorouracil and oxaliplatin, comprising screening a nucleic acid sequence at codon 118 of the ERCC1 gene isolated from a cell or tissue sample isolated from said patient for a nucleic acid sequence present at codon 118 of the ERCC1 gene, wherein the presence of the genotype (C/T) or (T/T) at codon 118 of the ERCC1 gene determines that said patient is likely to experience shorter survival following treatment with said therapy as compared to patients receiving the therapy not having the genotype (C/T) or (T/T).

6. The method of claim 5, wherein the therapy further comprises radiation therapy.

7. A method for treating a human metastatic colorectal cancer patient selected for therapy based on the presence of a genotype (C/C) at codon 118 of the ERCC1 gene, comprising administering an effective amount of a therapy comprising 5-Fluorouracil and oxaliplatin to the patient, wherein the patient was identified by a method comprising screening a sample isolated from the patient for the genotype at codon 118 of the ERCC1 gene, thereby treating the patient.

8. The method of claim 7, wherein the therapy further comprises radiation therapy.

9. The method of claim 1, wherein the method comprises screening a nucleic acid sequence at codon 118 of the ERCC1 gene in a cell or tissue sample isolated from said patient, wherein the therapy is selected for the patient based on the presence of the genotype (C/C) at codon 118 of the ERCC1 gene in the sample.

10. The method of claim 1, wherein the method comprises screening a nucleic acid sequence at codon 118 of the ERCC1 gene in a cell or tissue sample isolated from said patient, wherein the therapy is not selected for the patient based on the presence of the genotype (C/T) or (T/T) at codon 118 of the ERCC1 gene in the sample.

11. The method of any one of claims 1, 3, 5, 7, 9 or 10, wherein the sample is selected from the group consisting of bodily fluid, blood, a dry sample, hair, skin, a fixed sample, a frozen sample, a biopsy and a resection.

12. The method of any one of claims 1, 3, 5, 7, 9 or 10, wherein the nucleic acid is screened by at least one method of the group: polymerase chain reaction analysis (PCR), sequencing analysis, restriction enzyme analysis, mismatch cleavage analysis, single strand conformation polymorphism analysis, denaturing gradient gel electrophoresis, selective oligonucleotide hybridization, selective PCR amplification, selective primer extension, oligonucleotide ligation assay, exonuclease-resistant nucleotide analysis, Genetic Bite Analysis or primer-guided nucleotide incorporation analysis.

* * * * *

UNITED STATES PATENT AND TRADEMARK OFFICE
CERTIFICATE OF CORRECTION

| | | |
|---|---|---|
| PATENT NO. | : 7,662,553 B2 | Page 1 of 1 |
| APPLICATION NO. | : 10/522664 | |
| DATED | : February 16, 2010 | |
| INVENTOR(S) | : Lenz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this

Twenty-eighth Day of December, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

```
gtttgaagaa tttgagccaa acc                                          23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcttctgca cacttggcac                                              20
```